US006706283B1

(12) United States Patent
Appel et al.

(10) Patent No.: US 6,706,283 B1
(45) Date of Patent: Mar. 16, 2004

(54) CONTROLLED RELEASE BY EXTRUSION OF SOLID AMORPHOUS DISPERSIONS OF DRUGS

(75) Inventors: Leah E. Appel, Bend, OR (US); William J. Curatolo, Niantic, CT (US); Scott M. Herbig, East Lyme, CT (US); James A. S. Nightingale, Bend, OR (US); Avinash G. Thombre, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/495,061

(22) Filed: Jan. 31, 2000

Related U.S. Application Data
(60) Provisional application No. 60/119,406, filed on Feb. 10, 1999.

(51) Int. Cl.[7] ............ A61K 9/20; A61K 9/26; A61K 9/24; A61K 9/28; A61K 9/36
(52) U.S. Cl. ........... 424/473; 424/464; 424/465; 424/471; 424/472; 424/474; 424/479; 424/480
(58) Field of Search ............... 424/464, 465, 424/474, 480, 489, 468, 471, 472, 473, 479

(56) References Cited

U.S. PATENT DOCUMENTS

| 4,327,725 A | * | 5/1982 | Cortese et al. | 128/260 |
| 4,612,008 A | | 9/1986 | Wong et al. | 604/892 |
| 4,624,848 A | | 11/1986 | Lee | 424/22 |
| 4,851,232 A | * | 7/1989 | Urquhart et al. | 424/469 |
| 4,857,336 A | | 8/1989 | Khanna et al. | 424/473 |
| 4,983,593 A | | 1/1991 | Miyajima et al. | 514/110 |
| 4,992,278 A | | 2/1991 | Khanna | 424/473 |
| 5,035,897 A | * | 7/1991 | Ayer et al. | 424/473 |
| 5,128,145 A | * | 7/1992 | Edgren et al. | 424/473 |
| 5,456,923 A | | 10/1995 | Nakamichi et al. | 424/489 |
| 5,516,527 A | * | 5/1996 | Curatolo | 424/461 |
| 5,736,159 A | * | 4/1998 | Chen et al. | 424/480 |
| 5,837,379 A | | 11/1998 | Chen et al. | 424/465 |
| 6,147,072 A | * | 11/2000 | Bymaster et al. | 514/220 |
| 6,224,907 B1 | | 5/2001 | Davar et al. | 424/473 |

FOREIGN PATENT DOCUMENTS

| CA | 1330886 | 7/1994 | A01N/25/08 |
| EP | 0344603 | 12/1989 | A61K/31/675 |
| EP | 0552708 | 7/1993 | A61K/9/14 |
| EP | 0901786 | 3/1999 | A61K/9/14 |
| WO | WO9311749 | 6/1993 | A61K/9/10 |
| WO | WO9702017 | 1/1997 | A61K/9/14 |

OTHER PUBLICATIONS

XP–002121600, vol. 53, No. 4, 1983.
Santus, et al., Journal of Controlled Release, 35, 1995, 1021.
Chowdary et al., 32 Indian Drugs 477–483 (1995).
Dangprasirt et al., 21 Drug Development & Ind. Pharm. 2323 (1995).
Goracinova et al., 22 Drug Development & Ind. Pharm. 255 (1996).
James L. Ford, *The Current Status of Solid Dispersions*, 61 Pharm. Acta Helv. 69–88, 1986.

* cited by examiner

Primary Examiner—Thurman K. Page
Assistant Examiner—S. Tran
(74) *Attorney, Agent, or Firm*—Peter C. Richardson; Gregg C. Benson; James T. Jones

(57) ABSTRACT

Controlled release dosage forms for low solubility drugs are disclosed wherein an amorphous solid dispersion of the drug is coated with a non-dissolving and non-eroding coating that controls the influx of water to the core so as to cause extrusion of a portion of the core, as well as a method of treating a disease or disorder comprising administering such dosage form to a person.

71 Claims, 5 Drawing Sheets

CONTROLLED RELEASE BY EXTRUSION OF SOLID AMORPHOUS DISPERSIONS OF DRUGS

The priority date of Provisional Application Serial No. 60/119,406 filed Feb. 10, 1999 is claimed.

BACKGROUND OF THE INVENTION

The bioavailability of sparingly water-soluble drugs is well-known to be limited and to be profoundly affected by such factors as the fed state of the patient, the rate of metabolism in relation to the rate of absorption in the gastrointestinal (GI) tract, and the dosage form. Many attempts have been made to improve the form of dosage for such low solubility drugs, generally with the aim to improving the bioavailability of such drugs. Most such formulations were immediate release in nature as this generally maximizes the amount of drug absorbed. In a few cases, sustained or delayed release dosage forms have been formulated with a view to attaining a constant rate of release of the drug in the gut over a sufficiently sustained period of time. However, most such attempts have been unsuccessful, resulting in dosage forms that generally either provide immediate release only or poor bioavailability.

Exemplary sustained release dosage forms have included an osmotic tablet comprising a semipermeable wall surrounding a compartment containing the drug and a layer of swellable hydrogel, with the crystalline drug being delivered through a passageway in the semipermeable wall by swelling of the hydrogel, as described in U.S. Pat. No. 4,327,725; another osmotic tablet comprising a wall permeable to an exterior fluid but impermeable to the drug, the wall surrounding a compartment containing two osmotic agents, two expandable polymers and the drug, as described in U.S. Pat. No. 4,612,008; drug dispersed in a swellable hydrogel matrix core that releases the drug by diffusion into the environment of use, as described in U.S. Pat. No. 4,624,848; a hydrogel reservoir containing a multiplicity of tiny pills wherein each tiny pill consists of a wall surrounding a drug core, as described in U.S. Pat. No. 4,851,232; and a two-layered tablet wherein one layer is drug mixed with a hydrogel and the other layer is a hydrogel, as described in U.S. Pat. No. 5,516,527. One sustained release dosage form consists of a coated tablet with a core of a solid dispersion of drug in a swellable polyoxamer hydrogel that releases the drug by diffusion from the swollen tablet mass and by erosion of the tablet surface, as described in PCT Application No. 97/02017.

Solid dispersion dosage forms may be formed by solvent evaporation, by spray drying, by spraying drug solution onto the carrier in a fluidized bed granulator, by twin screw extrusion, by melt fusion, by mechanical admixture such as by ball milling and by mechanical admixture at an elevated but non-melting temperature. See, for example, PCT Application No. 93/11749; European Patent Application No. 0 552 708; U.S. Pat. No. 5,456,923; Chowdary et al., 32 Indian Drugs 477 (1995); Dangprasirt et al., 21 Drug Development & Ind. Pharm. 2323 (1995); and Goracinova et al., 22 Drug Development & Ind. Pharm. 255 (1996).

However, such solid dispersion drug delivery systems have achieved very limited success in delivering poorly water-soluble drugs as they generally tend to be immediate release forms having those forms' inherent drawbacks of high peak drug concentrations in the blood, short times following administration when drug concentrations in the blood reach a maximum ("$t_{max}$") and relatively short duration of effective levels of concentration in the blood. In addition, although improved bioavailability relative to crystalline drug is reported, bioavailability for such dosage forms is nevertheless often low in an absolute sense. Specifically, such drug delivery systems often exhibit little overall improvement in the concentration of drug in a patient's blood over a given time period (commonly referred to as "AUC" in reference to the calculation of the area under a curve comprising a plot of concentration of drug against time).

In the case of the solid polyoxamer dispersion dosage form reported in PCT 97/02017, the dosage form suffers either from slow and incomplete release in cases when drug is released by diffusion through a membrane coating due to the inherent low solubility of the drug; conversely, where drug is released from such a dosage form by erosion of the polyoxamer, drug release is non-zero order and variable, being dependent on the patient's fed state and gastric retention time. In addition, since the polyoxamer dispersion polymers disclosed are highly hydrophilic and generally require aqueous solvents for dissolution, these polymers cannot be used to form dispersions with hydrophobic drugs via solvent processing as it is difficult or impossible to dissolve the drug and polymer in a common solvent.

There is therefore still a need in the art for a controlled release dosage form for delivery of a low solubility drug with a short elimination half-life that provides improved drug bioavailability. These needs and others which will become apparent to one skilled in the art are met by the present invention, which is summarized and described in detail below.

BRIEF SUMMARY OF THE INVENTION

The present invention comprises a controlled release dosage form having two components: (a) a core containing a low solubility drug in the form of an amorphous solid dispersion; and (b) a non-dissolving and non-eroding coating surrounding the core, the coating controlling the influx of water to the core from an aqueous environment of use so as to cause drug release by extrusion of some or all of the core to the environment of use. At least a major portion of the drug, i.e., at least about 60% is amorphous (as opposed to crystalline). More preferably, substantially all of the drug, i.e., at least about 75%, is amorphous. Most preferably, essentially all of the drug, i.e., at least about 90% is amorphous. The term "drug" is conventional, denoting a compound having beneficial, prophylactic, and/or therapeutic properties when administered to an animal, especially a human.

DETAILED DESCRIPTION OF THE INVENTION

Figure 1:
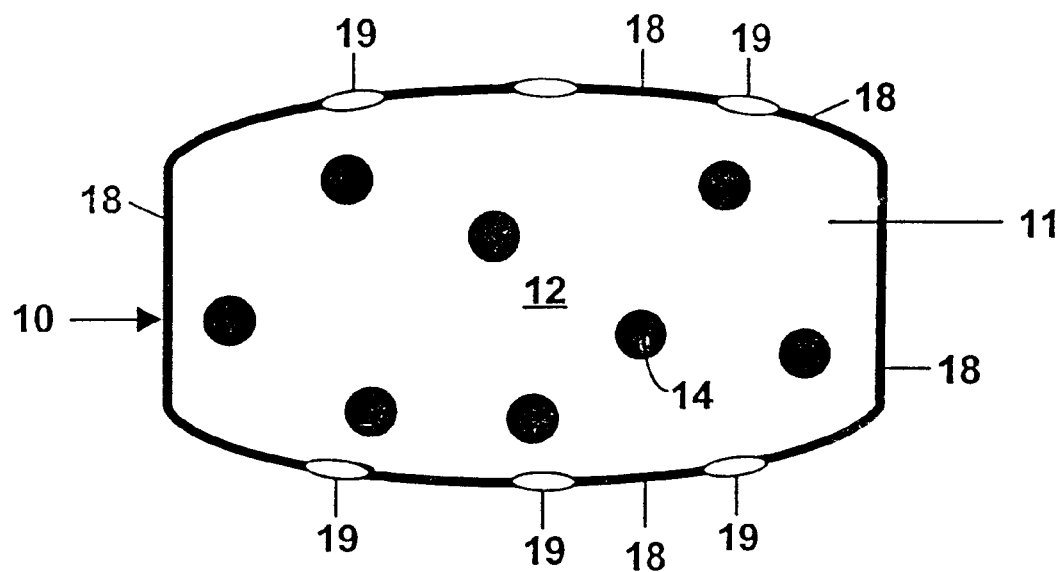
FIGS. 1–4 are schematics of exemplary embodiments of the invention.

According to the present invention there is provided a dosage form specifically designed to provide controlled release by an extrusion-type mechanism of a "low solubility" (defined below) drug that utilizes a core of such a drug in the form of a solid dispersion wherein a major portion of the drug is in an amorphous form. As used herein, the term "a major portion" of the drug means that at least 60% of the drug in the dispersion is in the amorphous form, rather than the crystalline form. Preferably, the drug in the dispersion is substantially amorphous. As used herein, "substantially amorphous" means that the amount of the drug in crystalline form does not exceed 25% as measured by powder X-ray diffraction analysis or by differential scanning calorimetry or by any other standard quantitative measurement. More preferably, the drug in the dispersion is essentially amorphous. As used herein, "essentially amorphous" means that the amount of the drug in crystalline form does not exceed 10% as measured by the methods previously described.

The term "extrusion" as it relates to the drug delivery mechanism is intended to convey an expulsion or forcing out of some or all of the core through at least one delivery port. By "at least one delivery port" is meant one or more holes, slits, passageways, channels or pores that may range in size from 0.1 to more than 2000 µm in diameter that permit release of drug from the dosage form. The drug may be delivered by the extrusion either in the form of a suspension of solids in water or primarily as a solution of the drug, to the extent dissolution has taken place in the core.

The form of the device may be any conventional form, including a tablet, a capsule, a caplet, a bead, a multiparticulate, powders for suspension or unit dosage packages or combinations thereof, and is generally useful in mammals and particularly useful for therapeutic uses in humans. Drug is released to the environment of use such as the gastro-intestinal (GI) tract as a result of the influx of water into the core and the resulting extrusion of an aqueous solution or suspension of the drug through one or more delivery ports or pores in the coating. The solid amorphous drug dispersion can either (1) dissolve in the core and be delivered primarily as a solution; or (2) be delivered as a solid suspension and dissolve in the GI tract following delivery. Since the solubility of a given drug is often pH-dependent, the device of the present invention is appropriate for delivery of any drug the solubility of which falls into the ranges noted herein.

Reference to the "release" of drug as used herein means (1) transport of drug from the interior of the dosage form to its exterior when the dosage form is a tablet, or from the interior to the exterior of the beads or granules when the dosage form includes multiparticulates, such that it contacts the fluid within a mammal's GI tract following delivery or (2) transport of drug from the interior of the dosage form such that it contacts a test medium for evaluation of the dosage form by an in vitro test. Reference to a "use environment" can thus be either to in vivo GI fluids or to an in vitro test medium. "Introduction" to a use environment includes either by ingestion or swallowing or use of implants or suppositories, where the use environment is in vivo, or being placed in a test medium where the use environment is in vitro.

The device comprises essentially two components: (1) a drug- and osmotic agent-containing core; and (2) a coating. The core comprises an amorphous solid dispersion of drug that contains an osmotic agent such as one or more osmogens and/or osmopolymers, and optionally contains solubility-enhancing agents and other excipients. The coating is preferably polymeric, is water-permeable, has at least one delivery port therein and does not dissolve or erode in the environment of use.

The dosage form of the present invention generally provides controlled delivery of the drug and in turn (1) the bioavailability of the drug is enhanced relative to a comparable dosage form where the drug is present in its undispersed state and (2) the time at which a maximum drug concentration ($C_{max}$) in an in vitro or in vivo environment of use is attained is delayed by from 30 minutes to 24 hours. By "undispersed" is meant that the drug is not formed into a solid amorphous dispersion. Rather, undispersed drug is simply the crystalline drug alone in its thermodynamically most stable form unless a crystalline form of the drug is unknown, in which case the control is the amorphous drug alone.

More specifically, the dosage forms of the invention provide one or more of the following features: (1) they provide a $C_{max}$, in an aqueous environment in vitro test, which is at least 1.2-fold that achieved by an identical controlled release dosage form containing the same quantity of undispersed drug; (2) they provide a $C_{max}$ in an aqueous environment in vitro test, at a time ($t_{max}$) which is at least 30 minutes longer but not more than 24 hours longer than the $t_{max}$ observed when the solid dispersion is tested without incorporation into a sustained release dosage form; (3) they provide an AUC in an aqueous in vitro test which is at least 1.25-fold that achieved by an identical controlled release dosage form containing the same amount of undispersed drug; (4) when dosed to a human or other animal they provide a drug $C_{max}$ in the blood that is achieved at a time $t_{max}$ which is at least 30 minutes longer than observed when a control composition is dosed, the control composition comprising the drug dispersion alone, i.e., not formulated in a sustained release dosage form; (5) when dosed to a human or other animal they provide a drug $C_{max}$ in the blood that is at least 1.25-fold that observed when a control composition is dosed, the control composition being identical to the test composition with the exception that the drug is undispersed before formulation into a sustained release dosage form; and (6) when dosed to a human or other animal they provide an AUC in drug concentration in the blood that is at least 1.25-fold that observed when a control composition is dosed, the control composition being the same as that described in (5) above.

The dosage forms of the present invention can be evaluated in vitro by placing the dosage form into a test medium such that if all the drug dissolved, this theoretical concentration would exceed the equilibrium concentration of the undispersed drug in the same test medium by a factor of at least 2. The concentration of dissolved drug is typically measured as a function of time by sampling the drug and plotting concentration versus time so that the $C_{max}$ can be ascertained. To avoid drug particulates which would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10–40%) than that obtained with the filter specified above but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Dosage forms of the present invention can also be tested in vivo in animals or humans using conventional methods for making such a determination. An in vivo test, such as a crossover study, may be used to determine whether a test dosage form provides an enhanced drug concentration in the blood (serum or plasma) versus time area under the curve (AUC in vivo) for a test subject dosed with the test dosage form relative to the AUC in vivo for a test subject dosed with a control dosage form as described above. In an in vivo crossover study a "test dosage form" is dosed to half a group of 12 or more humans and, after an appropriate washout period (e.g., one week) the same subjects are dosed with a "control dosage form" that comprises an equivalent quantity of undispersed drug as the "test dosage form." The other half of the group is dosed with the control dosage form first, followed by the test dosage form. The bioavailability is measured as the AUC determined for each group. AUC in vivo determinations can be made by plotting the blood serum or blood plasma concentration of drug along the ordinate (y-axis) versus time along the abscissa (x-axis). Generally, AUC in vivo values represent a number of values taken from all of the subjects in a patient test population and are, therefore, mean values averaged over the entire test population. By measuring the AUC in vivo for a population to which the test dosage form has been administered and comparing it with the AUC in vivo for the same population to which the dosage form has been administered, the test dosage form can be evaluated. The determination of AUCs is a well-known procedure and is described, for example, in the same Welling ACS Monograph mentioned above.

Four exemplary dosage form arrangements are schematically shown in FIGS. 1–4.

FIG. 1 depicts a "granular core" tablet 10 comprising a core 12, a coating 18 and at least one delivery port 19. The core comprises a drug-containing composition 11, and multiple granules of sweller-containing composition 14 mixed throughout the drug-containing composition 11.

Figure 2:
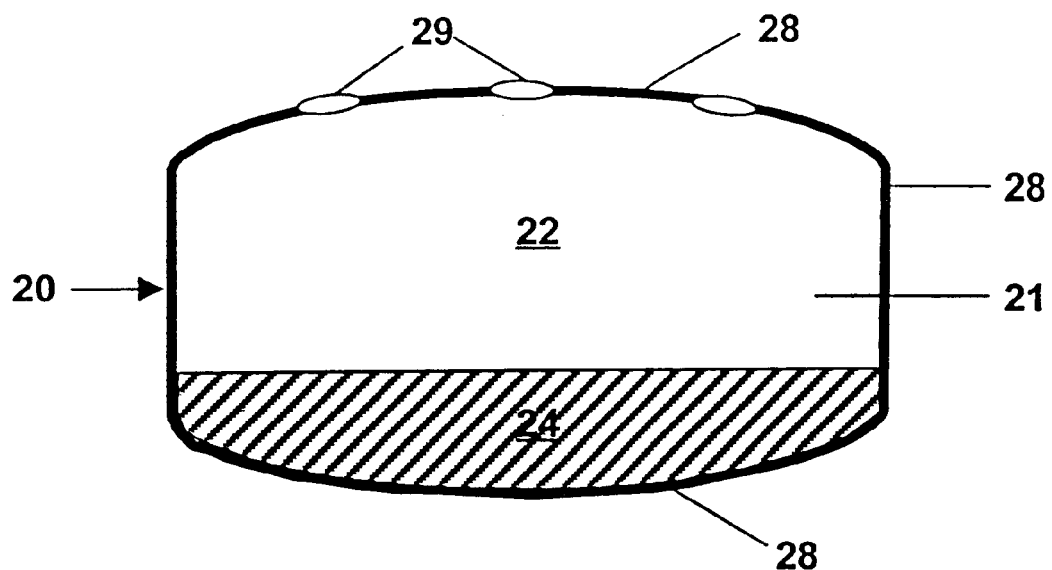

FIG. 2 depicts a "bi-layer" tablet 20 comprising a core 21 that has a drug layer composition 22 and a sweller layer composition 24 and, surrounding the core, a coating 28 that has at least one delivery port 29 through the coating connecting the drug layer 22 with the exterior of the dosage form.

Figure 3:
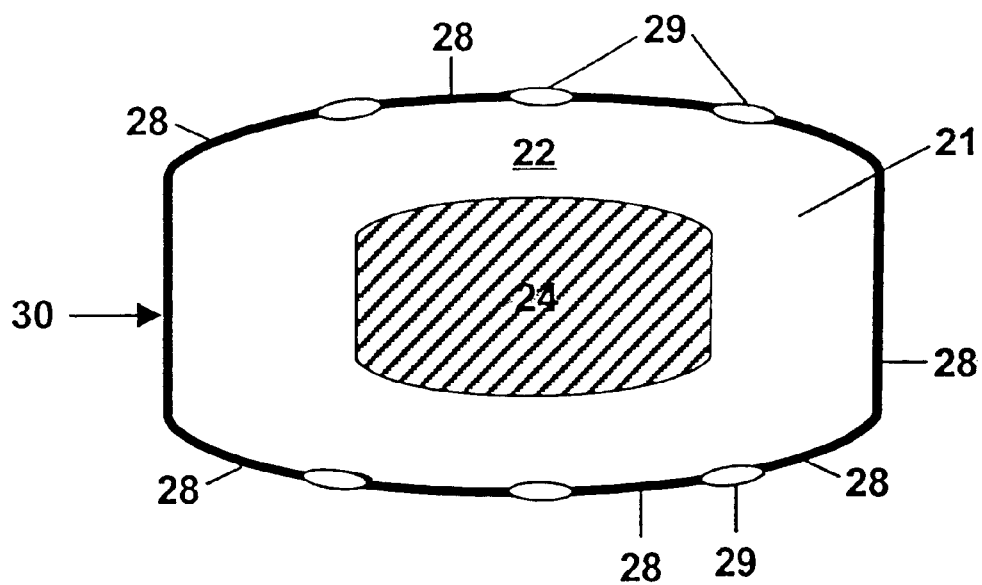

FIG. 3 depicts a "concentric core" tablet 30 comprising a core 21 that has a drug layer composition 22 that surrounds a sweller layer composition 24 and surrounding the core, a coating 28 that has at least one delivery port 29 through the coating connecting the drug layer 22 with the exterior of the dosage form.

Figure 4:
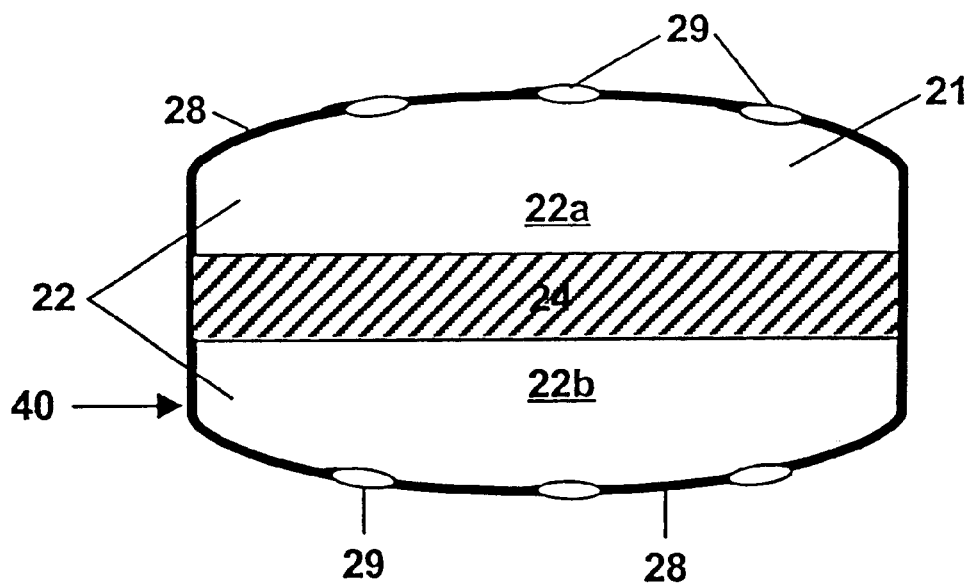

FIG. 4 depicts a "tri-layer" tablet 40 comprising a core 21 that has two drug layer compositions 22a and 22b on either side of a sweller layer composition 24 and, surrounding the core, a coating 28 that has at least one delivery port 29 through the coating connecting each drug layer 22a and 22b with the exterior of the dosage form.

The Drug

Prior to formation of the dispersion the drug in its pure state may be crystalline or amorphous, but when dispersed in the solid dispersion polymer a major portion of the drug is preferably in an amorphous or non-crystalline state, such that its non-crystalline nature is demonstrable by X-ray diffraction analysis or by differential scanning calorimetry. The dispersion may contain from about 5 to 90 wt % drug, preferably 20 to 70 wt %.

The drug is a "low-solubility drug," meaning that the drug has a minimum aqueous solubility of about 40 mg/mL or less at a physiologically relevant pH (e.g., pH 1–8). Thus, the drug may be either substantially water-insoluble, meaning that the drug has a minimum water solubility of less than 10 micrograms/mL at a physiologically relevant pH or sparingly water-soluble, that is, has a minimum aqueous solubility of about 10 micrograms/mL up to about 1 to 2 mg/mL, or even moderate solubility, such as a minimum aqueous solubility as high as about 20 to 40 mg/mL. In general, it may be said that the drug has a dose-to-aqueous solubility ratio greater than about 5 mL, where the drug solubility is the minimum value observed in any physiologically relevant aqueous solution, including unbuffered water and USP simulated gastric and intestinal buffered solutions. In some cases, it is also desirable to enhance the solubility of the drug within the dosage form to increase the rate of release from the dosage form or to improve the absorption of drug in the colon. In such cases, the invention may be applied to drugs with solubility as high as 20 to 40 mg/mL. This is particularly true when it is desired to deliver a solution of the drug. In such cases, the dose-to-aqueous solubility ratio may be as low as 1 mL.

Virtually any beneficial therapeutic agent that meets the solubility criteria may be used as the drug in the present invention. In addition, the drug may be employed in the form of its pharmaceutically acceptable salts as well as in anhydrous, hydrated, and solvated forms and in the form of prodrugs.

Preferred classes of drugs include, but are not limited to, antihypertensives, antianxiety agents, antidepressants, barbituates, anticlotting agents, anticonvulsants, blood glucose-lowering agents, decongestants, antihistamines, antitussives, antineoplastics, beta blockers, antiinflammatories antipsychotic agents, cognitive enhancers, cholesterol-reducing agents, antiobesity agents, autoimmune disorders agents, anti-impotence agents, antibacterial and antifungal agents, hypnotic agents, anti-Parkinsonism agents, anti-Alzheimer's Disease agents, antibiotics and antiviral agents.

Specific examples of the above and other classes of drugs and therapeutic agents deliverable by the invention are set forth below, by way of example only. Specific examples of antihypertensives include prazosin, nifedipine, trimazosin and doxazosin; a specific example of a blood glucose-lowering agent is glipizide; a specific example of an anti-impotence agent is sildenafil citrate; specific examples of antineoplastics include chlorambucil, lomustine and echinomycin; a specific example of an imidazole-type antineoplastic is tubulazole; specific examples of antiinflammatory agents include betamethasone, prednisolone, aspirin, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir and virazole; specific examples of vitamins/nutritional agents include retinol and vitamin E; specific examples of a beta blockers include timolol and nadolol; a specific example of an emetic is apomorphine; specific examples of a diuretic include chlorthalidone and spironolactone; a specific example of an anticoagulant is dicumarol; specific examples of cardiotonic include digoxin and digitoxin; specific examples of androgens include 17-methyltestosterone and testosterone; a specific example of a steroidal hypnotic/anesthetic is alfaxalone; specific examples of anabolic agents include fluoxymesterone and methanstenolone; specific examples of antidepression agents include sulpiride, fluoxetine, paroxetine, venlafaxine, sertraline, [3,6-dimethyl-2-(2,4,6-trimethyl-phenoxy)-pyridin-4-yl]-(1-ethylpropyl)-amine and 3,5-dimethyl-4-(3'-pentoxy)-2-(2',4',6'-trimethylphenoxy)pyridine; specific examples of antibiotics include ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole and griseofulvin; specific examples of anthelmintic agents include thiabendazole and oxfendazole; specific examples of antihistamines include astemizole, levocabastine, cetirizine and cinnarizine; specific examples of antipsychotics include fluspirilene, penfluridole and ziprasidone; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include tetracycline and minocycline; specific examples of a macrolide antibiotics include azithromycin, clarithromycin, erythromycin and spiramycin; specific examples of glycogen phosphorylase inhibitors include [R-(R*S*)]-5-chloro-N-[2-hydroxy-3-[methoxymethylamino}-3-oxo-1-(phenylmethyl)propyl]propyl]-1H-indole-2-carboxamide and 5-chloro-1H-indole-2-carboxylic acid [(1S)-benzyl-3-((3R,4S)-dihydroxypyrrolidin-1-yl-)-(2R)-hydroxy-3-oxypropyl]amide.

Still further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride and doxepin hydrochloride, the anti-hypertensive amlodipine besylate, the antiinflammatories iroxicam, valdecoxib and celicoxib, and the antibiotics carbenicillin indanyl sodium, becampicillin hydrochloride, troleandomycin and doxycycline hyclate.

The Dispersion Polymer

Suitable polymers for forming the solid dispersion of drug are preferably polymeric, concentration-enhancing, non-aqueous solvent-processable and inert. By "non-aqueous solvent" is meant solvents comprising <30 wt % water.

By "non-aqueous solvent-processable" is meant the polymer is capable of being processed with the drug in a common non-aqueous solvent to form the solid dispersion, i.e., it is generally adaptable to techniques utilizing non-aqueous solvents in the formation of solid dispersions. Such techniques include evaporation, spray-drying, or spray coating. The polymer has a preferred solubility in the non-aqueous solvent of at least 0.1 mg/mL, more preferably greater than 1 mg/mL and most preferably greater than 10 mg/mL. This property is critical for forming the solid amorphous dispersion of the drug and dispersion polymer via solvent processing as the drug and dispersion polymer must be dissolved in a common solvent and such solvents cannot be substantially aqueous as the drugs by definition have a relatively low aqueous solubility.

Such dispersion polymers are aqueous-soluble in the sense that they are sufficiently soluble (21 mg/mL) in at least a portion of the 1 to 8 pH range that they exhibit a "concentration enhancing" property. By "concentration-enhancing" is meant the concentration of the pure drug in aqueous media is substantially increased when formed into a solid dispersion with the polymer, the concentration enhancement being on the order of at least 20%.

By "inert" is meant not adversely reactive or bioactive, yet still capable of positively affecting the drug's bioavailability.

The amount of the polymer present in the dispersion generally ranges from about 10 to about 95 wt %, preferably 30 to 80 wt %.

A preferred class of polymers comprises ionizable and nonionizable cellulosic polymers (including those with ether or ester or a mixture of ester/ether substituents and copolymers thereof, including both so-called "enteric" and "non-enteric" polymers); and vinyl polymers and copolymers having substituents of hydroxyl, alkylacyloxy and cyclicamido.

Exemplary ionic cellulosics include carboxymethylcellulose (CMC) and its sodium salt, carboxyethylcellulose (CEC), hydroxyethylmethylcellulose acetate phthalate, hydroxyethylmethylcellulose acetate succinate, hydroxypropylmethylcellulose phthalate (HPMCP), hydroxypropylmethylcellulose succinate, hydroxypropylcellulose acetate phthalate (HPCAP), hydroxypropylcellulose acetate succinate (HPCAS), hydroxypropylmethylcellulose acetate phthalate (HPMCAP), hydroxypropylmethylcellulose acetate succinate (HPMCAS), hydroxypropylmethylcellulose acetate trimellitate (HPMCAT), hydroxypropylmethylcellulose acetate phthalate (HPMCAP), hydroxypropylcellulose butyrate phthalate, carboxymethylethylcellulose and its sodium salt, cellulose acetate phthalate (CAP), methylcellulose acetate phthalate, cellulose acetate trimellitate (CAT), cellulose acetate terephthalate, cellulose acetate isophthalate, cellulose propionate phthalate, cellulose propionate trimellitate, cellulose butyrate trimellitate and mixtures thereof.

Exemplary nonionic cellulosics include methylcellulose (MC), ethyl cellulose (EC), hydroxyethyl cellulose (HEC), hydroxypropylcellulose (HPC), hydroxypropylmethylcellulose (HPMC), hydroxypropylmethylcellulose acetate, hydroxyethylmethylcellulose, hydroxyethylcellulose acetate, hydroxyethylethylcellulose and mixtures thereof.

Exemplary vinyl polymers and copolymers useful as concentration-enhancing dispersion polymers include methacrylic acid copolymers, aminoalkyl methacrylate copolymers, carboxylic acid functionalized polymethacrylates, and amine-functionalized polymethacrylates, poly(vinyl acetal) diethylaminoacetate, polyvinyl pyrrolidone (PVP), polyvinyl alcohol (PVA), polyvinyl alcohol/polyvinyl acetate (PVA/PVAc) copolymers and mixtures thereof.

Other useful dispersion polymers include polyethylene glycol/polypropylene glycol (PEG/PPG) copolymers, polyethylene/polyvinyl alcohol (PE/PVA) copolymers, dextrin, pullulan, acacia, tragacanth, sodium alginate, propylene glycol alginate, agar powder, gelatin, starch, processed starch, glucomannan, chitosan and mixtures thereof.

Particularly preferred dispersion polymers are PVA, PVP, PVA/PVAc copolymers and cellulosic polymers that are aqueous-soluble over at least a portion of the pH range 1<pH<8, including HPMC, HPMCP, HPMCAS, CAP, CAT and mixtures thereof.

The Dispersion

The amorphous solid dispersion of drug may be prepared by any of the known ways mentioned above, including, for example, by melt fusion, by mechanical processing such as in a twin-screw extruder or in a ball mill, or by solvent processing. When the dispersion is made by mechanical means such as by ball milling or extrusion, a major portion (>60%) of the drug is typically in an amorphous state, with the remaining portion remaining in a crystalline state. When prepared by solvent processing, a major portion of the drug is virtually always in an amorphous state, usually substantially all (>75%) is in that state, and often essentially all (>90%) of the drug is in an amorphous state. By "amorphous state" is meant the drug may be present in the dispersion in any of three broad classes of forms: (a) in discrete, drug-rich domains; (b) homogeneously distributed therein, i.e., a solid solution; or (c) any state or combination of states between the extremes of (a) and (b).

In solvent processing, a homogeneous solution of drug and the dispersion polymer is formed, alone or along with other excipients that may or may not be dissolved, followed by solvent removal by precipitation or evaporation. Precipitation is typically induced by contacting the drug/dispersion polymer solution with a non-solvent such as water, a liquid hydrocarbon or super-critical $CO_2$. A preferred method of forming the dispersion is by dissolving the drug and dispersion polymer in a common solvent, then removing the solvent by spray-drying the mixture. Spray-drying and spray-coating processes and equipment are described generally in *Perry's Chemical Engineers' Handbook*, pages 20–54 to 20–57 (6th Ed. 1984). More details on spray-drying processes and equipment are reviewed by Marshal in 50 *Chem. Eng. Prog. Monogr.* series 2 (1954).

The terms "spray-drying" and "spray-coating" in connection with the present invention are used conventionally and broadly refer to processes involving breaking up liquid mixtures into small droplets (atomization) and rapidly removing solvent from the mixtures in a vessel such as a spray-drying apparatus or a fluidized bed- or pan-coater where there is a strong driving force for evaporation of solvent from the droplets. In the case of spray-coating the droplets impinge on a particle, bead, pill, tablet, or capsule, resulting in a coating comprising the solid amorphous dispersion. Spray-coating may also be conducted on a metal, glass or plastic surface and the coated layer may subsequently be removed and milled to the desired particle size. In the case of spray-drying, the droplets generally dry prior to impinging on a surface, thus forming particles of solid amorphous dispersion on the order of 1 to 100 micrometers in diameter. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both (1) and (2). For example, a solution of drug and a dispersion polymer such as HPMCAS in acetone may be suitably spray-dried by spraying the solution at a temperature of 50° C. (the vapor pressure of acetone at 50° C. is about 0.8 atm) into a chamber held at 0.01 to 0.2 atm total pressure by connecting the outlet to a vacuum pump. Alternatively, such a solution may be sprayed into a chamber where it is mixed with nitrogen gas at a temperature of 80° C. to 250° C. and pressure of 1.0 to 1.2 atm.

Generally, the temperature and flow rate of the drying gas is chosen so that dispersion polymer/drug solution droplets are dry enough by the time they reach the wall of the apparatus that they are essentially solid, so that they form a fine powder and do not stick to the apparatus wall. The actual length of time to achieve this level of dryness depends on the size of the droplets. Droplet sizes generally are larger than about 1 μm in diameter, with 5 to 100 μm being typical. The large surface-to-volume ratio for the droplets and the large driving force for evaporation of solvent leads to actual drying times of a few seconds or less. For some mixtures of drug/dispersion polymer/solvent this rapid drying is critical to the formation of a relatively uniform, homogeneous composition as opposed to an undesirable separation into drug-rich and polymer-rich phases. Such dispersions having a homogenous composition can be considered solid solutions and may be supersaturated in drug.

Solidification times should be less than 100 seconds, preferably less than a few seconds, and more preferably less than 1 second. In general, to achieve such rapid solidification of the drug/polymer solution, it is preferred that the diameter of droplets formed during the spray-drying process are less then 100 μm, preferably less than 50 μm, and most preferably less than 25 μm. The so-formed solid particles resulting from solidification of these droplets generally tend to be 2 to 40 μm in diameter.

Following solidification, the solid powder typically remains in the spray-drying chamber for 5 to 60 seconds, evaporating more solvent. The final solvent content of the solid dispersion as it exits the dryer should be low, since low solvent content tends to reduce the mobility of drug molecules in the dispersion, thereby improving its stability. Generally, the residual solvent content of the dispersion should be less than 10 wt % and preferably less than 2 wt %.

The solution spray-dried to form the polymer/drug dispersion can be quite simple, containing only drug and polymer in a solvent. Typically, the weight ratio of polymer to drug in the solution ranges from 0.1 to 20 and preferably from 0.5 to 5. However, when the drug dose is low (less than 20 mg), the ratio may be even more than 5.

Other excipients may be added to the spray solution, either co-dissolved in the solvent along with the drug and dispersion polymer or suspended in the solution to form a slurry. Such excipients may include: acids, bases or buffers to modify the ionic state and dissolution properties of the resulting dispersion; fillers, binders, disintegrants or other materials to improve the tableting process or final properties of the tablet; antioxidants to improve the dispersion's stability; osmotic agents, including both osmotically effective solutes such as sugars, salts and polyols and water-swellable hydrophilic polymers; and surfactants to affect the wetting or dissolution rate of the tablet core.

Solvents suitable for spray-drying may be essentially any organic compound or mixtures of an organic compound and water in which the drug and polymer are mutually soluble. Because the invention utilizes low water solubility drugs, water alone is generally not a suitable solvent. However, mixtures of water and organic compounds are often suitable. Preferably, the solvent is also relatively volatile with a boiling point of 150° C. or less. However, in those cases where the solubility of the drug in the volatile solvent is low, it may be desirable to include a small amount, say 2 to 25 wt %, of a low volatility solvent such as N-methylpyrrolidone (NMP), dimethylsulfoxide (DMSO) or dimethylacetamide (DMAc) in order to enhance drug solubility. Preferred solvents include alcohols such as methanol, ethanol, n-propanol, isopropanol, and butanol; ketones such as acetone, methyl ethyl ketone and methyl isobutyl ketone; esters such as ethyl acetate and propylacetate; and various other solvents such as acetonitrile, methylene chloride, toluene, and 1,1,1-trichloroethane.

The Osmotic Agent

In addition to the solid amorphous drug dispersions, the core of the drug delivery device of the present invention includes an "osmotic agent." By "osmotic agent" is meant any agent which creates a driving force for transport of water from the environment of use into the core of the device. Exemplary osmotic agents are water-swellable hydrophilic polymers, and osmogens (or osmagens). Thus, the core may include water-swellable hydrophilic polymers, both ionic and nonionic, often referred to as "osmopolymers" and "hydrogels." The amount of water-swellable hydrophilic polymers present in the core may range from about 5 to about 80 wt %, preferably 10 to 50 wt %. Exemplary materials include hydrophilic vinyl and acrylic polymers, polysaccharides such as calcium alginate, PEO, PEG, PPG, poly(2-hydroxyethyl methacrylate), poly(acrylic) acid, poly (methacrylic) acid, PVP and crosslinked PVP, PVA, PVA/ PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, HEC, HPC, HPMC, CMC and CEC, sodium alginate, polycarbophil, gelatin, xanthan gum, and sodium starch glycolate. Other materials include hydrogels comprising interpenetrating networks of polymers which may be formed by addition or by condensation polymerization, the components of which may comprise hydrophilic and hydrophobic monomers such as those just mentioned. Preferred polymers for use as the water-swellable hydrophilic polymers include PEO, PEG, PVP, sodium croscarmellose, HPMC, sodium starch glycolate, polyacrylic acid and crosslinked versions or mixtures thereof. In one embodiment of the invention the osmotic agent and the dispersion polymer can comprise the same polymeric material.

By "osmotically effective solutes," is meant any water-soluble compound that is commonly referred to in the pharmaceutical arts as an "osmogen" or an "osmagent." The amount of osmogen present in the core may range from about 2 to about 70 wt %, preferably 10 to 50 wt %. Typical classes of suitable osmogens are water-soluble organic acids, salts and sugars that are capable of imbibing water to thereby effect an osmotic pressure gradient across the barrier of the surrounding coating. Typical useful osmogens include magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. Particularly preferred osmogens are glucose, lactose, sucrose, mannitol, xylitol and sodium chloride.

Other Core Components

Finally, the solid dispersion core may include a wide variety of additives and excipients that enhance drug solubility or that promote stability, tableting or processing of the dispersion. Such additives and excipients include tableting aids, surfactants, water-soluble polymers, pH modifiers, fillers, binders, pigments, disintegrants, antioxidants, lubricants and flavorants. Exemplary of such components are microcrystalline cellulose; metallic salts of acids such as aluminum stearate, calcium stearate, magnesium stearate, sodium stearate, and zinc stearate; fatty acids, hydrocarbons and fatty alcohols such as stearic acid, palmitic acid, liquid paraffin, stearyl alcohol, and palmitol; fatty acid esters such as glyceryl (mono- and di-) stearates, triglycerides, glyceryl (palmiticstearic) ester, sorbitan monostearate, saccharose monostearate, saccharose monopalmitate, and sodium stearyl fumarate; alkyl sulfates such as sodium lauryl sulfate and magnesium lauryl sulfate; polymers such as polyethylene glycols, polyoxethylene glycols, and polytetrafluoroethylene; and inorganic materials such as talc and dicalcium phosphate; sugars such as lactose and xylitol; and sodium starch glycolate.

The core may also include solubility-enhancing agents that promote the water solubility of the drug, present in an amount ranging from about 5 to about 50 wt %. Examples of suitable solubility-enhancing agents include surfactants; pH control agents such as buffers, organic acids and organic acid salts and organic and inorganic bases; glycerides; partial glycerides; glyceride derivatives; polyoxyethylene and polyoxypropylene ethers and their copolymers; sorbitan esters; polyoxyethylene sorbitan esters; carbonate salts; alkyl sulfonates; and cyclodextrins.

All such solubility-enhancing and other additives may be added directly to the spray-drying solution such that the additive is dissolved or suspended in the solution as a slurry. Alternatively, such additives may be added following the spray-drying process to aid in forming the final dosage form.

The Coating

The essential constraints on the coating are that it be water-permeable, have at least one port for the delivery of drug, and be non-dissolving and non-eroding during release of the drug formulation, such that drug is substantially entirely delivered through the delivery port(s) or pores as opposed to delivery primarily via permeation through the coating material itself. By "delivery port" is meant any passageway, opening or pore whether made mechanically, by laser drilling, by pore formation either during the coating process or in situ during use or by rupture during use. Coating should be present in an amount ranging from about 5 to 30 wt %, preferably 10 to 20 wt % relative to the core weight.

A preferred form of coating is a semipermeable polymeric membrane that has the port(s) formed therein either prior to or during use. Thickness of such a polymeric membrane may vary between about 20 and 800 $\mu$m, and is preferably in the range of 100 to 500 $\mu$m. The delivery port(s) should generally range in size from 0.1 to 3000 $\mu$m or greater, preferably on the order of 50 to 3000 $\mu$m in diameter. Such port(s) may be formed post-coating by mechanical or laser drilling or may be formed in situ by rupture of the coatings; such rupture may be controlled by intentionally incorporating a relatively small weak portion into the coating. Delivery ports may also be formed in situ by erosion of a plug of water-soluble material or by rupture of a thinner portion of the coating over an indentation in the core. In addition, delivery ports may be formed during coating, as in the case of asymmetric membrane coatings of the type disclosed in U.S. Pat. Nos. 5,612,059 and 5,698,220, the disclosures of which are incorporated by reference.

When the delivery port is formed in situ by rupture of the coating, a particularly preferred embodiment is a collection of beads that may be of essentially identical or of a variable composition. Drug is primarily released from such beads following rupture of the coating and, following rupture, such release may be gradual or relatively sudden. When the collection of beads has a variable composition, the composition may be chosen such that the beads rupture at various times following administration, resulting in the overall release of drug being sustained for a desired duration.

Coatings may be dense, microporous or "asymmetric," having a dense region supported by a thick porous region such as those disclosed in U.S. Pat. Nos. 5,612,059 and 5,698,220. When the coating is dense the coating is composed of a water-permeable material. When the coating is porous, it may be composed of either a water-permeable or a water-impermeable material. When the coating is composed of a porous water-impermeable material, water permeates through the pores of the coating as either a liquid or a vapor.

Examples of osmotic devices that utilize such dense coatings include U.S. Pat. Nos. 3,995,631 and 3,845,770, the disclosures of which pertaining to dense coatings are incorporated herein by reference. Such dense coatings are permeable to the external fluid such as water and may be composed of any of the materials mentioned in these patents as well as other water-permeable polymers known in the art.

The membranes may also be porous as disclosed in U.S. Pat. Nos. 5,654,005 and 5,458,887 or even be formed from water-resistant polymers. U.S. Pat. No. 5,120,548 describes another suitable process for forming coatings from a mixture of a water-insoluble polymer and a leachable water-soluble additive, the pertinent disclosures of which are incorporated herein by reference. The porous membranes may also be formed by the addition of pore-formers as disclosed in U.S. Pat. No. 4,612,008, the pertinent disclosures of which are incorporated herein by reference.

In addition, vapor-permeable coatings may even be formed from extremely hydrophobic materials such as polyethylene or polyvinylidenefluoride that, when dense, are essentially water-impermeable, as long as such coatings are porous.

Materials useful in forming the coating include various grades of acrylics, vinyls, ethers, polyamides, polyesters and cellulosic derivatives that are water-permeable and water-insoluble at physiologically relevant pHs, or are susceptible to being rendered water-insoluble by chemical alteration such as by crosslinking.

Specific examples of suitable polymers (or crosslinked versions) useful in forming the coating include plasticized, unplasticized and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMACT, poly(acrylic) acids and esters and poly(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes and synthetic waxes.

A preferred coating composition comprises a cellulosic polymer, in particular cellulose ethers, cellulose esters and cellulose ester-ethers, i.e., cellulosic derivatives having a mixture of ester and ether substituents, such as HPMCP.

Another preferred class of coating materials are poly (acrylic) acids and esters, poly(methacrylic) acids and esters, and copolymers thereof.

A more preferred coating composition comprises cellulose acetate. An even more preferred coating comprises a cellulosic polymer and PEG. A most preferred coating comprises cellulose acetate and PEG.

Coating is conducted in conventional fashion, typically by dissolving the coating material in a solvent and then coating by dipping, spray-coating or preferably by pan-coating. A preferred coating solution contains 5 to 15 wt % polymer. Typical solvents useful with the cellulosic polymers mentioned above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. Pore-formers and non-solvents (such as water, glycerol and ethanol) or plasticizers (such as diethyl phthalate) may also be added in any amount as long as the polymer remains soluble at the spray temperature. Pore-formers and their use in fabricating coatings are described in U.S. Pat. No. 5,612,059, the pertinent disclosures of which are incorporated herein by reference.

Coatings may also be hydrophobic microporous layers wherein the pores are substantially filled with a gas and are not wetted by the aqueous medium but are permeable to water vapor, as disclosed in U.S. Pat. No. 5,798,119, the pertinent disclosures of which are incorporated herein by reference. Such hydrophobic but water-vapor permeable coatings are typically composed of hydrophobic polymers such as polyalkenes, polyacrylic acid derivatives, polyethers, polysulfones, polyethersulfones, polystyrenes, polyvinyl halides, polyvinyl esters and ethers, natural waxes and synthetic waxes. Especially preferred hydrophobic microporous coating materials include polystyrene, polysulfones, polyethersulfones, polyethylene, polypropylene, polyvinyl chloride, polyvinylidene fluoride and polytetrafluoroethylene. Such hydrophobic coatings can be made by known phase inversion methods using any of vapor-quench, liquid quench, thermal processes, leaching soluble material from the coating or by scintering coating particles. In thermal processes, a solution of polymer in a latent solvent is brought to liquid-liquid phase separation in a cooling step. When evaporation of the solvent is not prevented, the resulting membrane will typically be porous. Such coating processes may be conducted by the processes disclosed in U.S. Pat. Nos. 4,247,498; 4,490,431 and 4,744,906, the disclosures of which are also incorporated herein by reference.

Another embodiment of sustained release osmotic dosage forms of this invention comprises an osmotic drug-containing tablet which is surrounded by an asymmetric membrane, where said asymmetric membrane possesses one or more thin dense regions in addition to less dense porous regions. This type of membrane, similar to those used in the reverse-osmosis industry, generally allows higher osmotic fluxes of water than can be obtained with a dense membrane.

When applied to a drug formulation, e.g. a tablet, such an asymmetric membrane allows high drug fluxes and well-controlled sustained drug release. This asymmetric membrane comprises a semipermeable polymeric material, that is, a material which is permeable to water, and substantially impermeable to salts and organic solutes such as drugs.

Materials useful for forming such an asymmetric semipermeable membrane include polyamides, polyesters and cellulose derivatives. Preferred are cellulose ethers and esters. Especially preferred are CA, CAB and EC. Especially useful materials include those which spontaneously form one or more exit passageways, either during manufacturing or when placed in an environment of use. These preferred materials comprise porous polymers, the pores of which are formed by phase inversion during manufacturing, as described above, or by dissolution of a water-soluble component present in the membrane.

The asymmetric membrane is formed by a phase-inversion process. The coating polymer, e.g., EC or CA, is dissolved in a mixed solvent system comprising a mixture of solvents (e.g., acetone) and non-solvents (e.g., water) for the polymer. The components of the mixed solvent are chosen such that the solvent (e.g. acetone) is more volatile than the non-solvent (e.g. water) When a tablet is contacted with such a solution and dried, the solvent component of the solvent mixture evaporates more quickly than the non-solvent. This change in solvent composition during drying causes the solution to separate into two phases so that, when solid, the polymer on the tablet is a porous solid with a thin dense outer region. This outer region possesses multiple pores through which drug can be delivered as a solution or a suspension of drug particles, which particles may be crystalline, amorphous or a drug/polymer dispersion.

In a preferred embodiment of an asymmetric membrane-coated tablet, the polymer/solvent/non-solvent mixture is sprayed onto a bed of tablets in a tablet-coating apparatus such as a Freund HCT-60 tablet coater. In this process, the tablet is coated with thick porous regions, and with a final outer thin dense region.

In the environment of use such as the GI tract, water is imbibed through the semipermeable asymmetric membrane into the tablet core. As soluble material in the tablet core dissolves, an osmotic pressure gradient across the membrane builds. When the hydrostatic pressure within the membrane enclosed core exceeds the pressure of the environment of use, the drug-containing solution is "pumped" out of the dosage form via the delivery port(s) through the semipermeable membrane. In addition the hydrostatic pressure may cause the formation of pores or even large delivery port(s) by rupture of a portion of the coating. The relatively constant osmotic pressure difference across the membrane results in a constant, well-controlled delivery of drug to the use environment. A portion of the drug dissolved in the tablet also exits via diffusion.

In this asymmetric-membrane-coated tablet embodiment, the drug may be incorporated into the dispersion in its neutral form or as a salt. It is often desirable to include one or more solubilizing excipients, such as ascorbic acid, erythorbic acid, citric acid, tartaric acid, glutamic acid, aspartic acid, glycerides, partial glycerides, glyceride derivatives, PEG, PEG esters, PPG esters, polyhydric alcohol esters, polyoxyethylene ethers, sorbitan esters, polyoxyethylene sorbitan esters, saccharide esters, phospholipids, polyethylene oxide-polypropylene oxide block co-polymers. Most preferred are the solubilizing excipients ascorbic acid, aspartic acid, citric acid, tartaric acid, glyceryl monocaprylate, glyceryl monostearate, glycerol monolaurate, and C8–C10 partial glycerides.

Use and Fabrication

In use, the solid dispersion core imbibes water through the coating from the environment of use such as the GI tract so as to increase the pressure within the core. The pressure difference between the core and the device's exterior drives the delivery of the core's contents. Because the coating remains intact, the drug formulation is extruded out of the core through the delivery port(s) into the environment of use, either primarily as a solution of drug or as a suspension of drug; when delivered as a suspension, the drug formulation subsequently dissolves in the GI tract.

A preferred embodiment of osmotic delivery devices consists of a drug layer containing the substantially amorphous drug/polymer dispersion and a sweller layer that comprises a water-swellable polymer, with a coating surrounding the drug and sweller layer. Each layer may contain other excipients such as tableting aids, osmagents, surfactants, water-soluble polymers and water-swellable polymers.

Such osmotic delivery devices may be fabricated in various geometries including bilayer, wherein the core comprises a drug layer and a sweller layer adjacent to each other; trilayer, wherein the core comprises a sweller layer "sandwiched" between two drug layers; and concentric, wherein the core comprises a central sweller composition surrounded by the drug layer.

The coating of such a tablet comprises a membrane permeable to water but substantially impermeable to drug and excipients contained within. The coating contains one or more exit passageways or ports in communication with the drug-containing layer(s) for delivering the drug dispersion composition. The drug-containing layer(s) of the core contains the drug dispersion composition (including optional osmagents and hydrophilic water-soluble polymers), while the sweller layer consists of an expandable hydrogel, with or without additional osmotic agents. Such delivery devices are exemplified in FIG. 4 and Example 3 (tri-layer), FIG. 2 and Example 4 (bi-layer) and in FIG. 3 and Example 5 (concentric).

When placed in an aqueous medium, the tablet imbibes water through the membrane, causing the composition to form a dispensable aqueous composition, and causing the hydrogel layer to expand and push against the drug dispersion-containing composition, forcing the composition out of the exit passageway. The composition can swell, aiding in forcing the drug out the passageway. Drug can be delivered from this type of delivery system either dissolved or dispersed in the composition that is expelled from the exit passageway.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

Exemplary materials useful in forming the drug dispersion-containing composition, in addition to the drug dispersion itself, include HPMC, PEO and PVP and other pharmaceutically acceptable carriers. In addition, osmagents such as sugars or salts, especially sucrose, lactose, xylitol, mannitol, or sodium chloride, may be added. Materials which are useful for forming the hydrogel layer include sodium CMC, PEO, poly(acrylic acid), sodium (polyacrylate), sodium croscarmelose, sodium starch glycolate, PVP, crosslinked PVP, and other high molecular weight hydrophilic materials. Particularly useful are PEO polymers having an average molecular weight from about 5,000,000 to about 7,500,000 daltons.

In general, the dosage form provides a maximum drug concentration (MDC) in a use environment that is at least 1.2-fold that of an equivalent control dosage form except that the drug is in undispersed form. When the dosage form contains homogeneous dispersions (which are preferred), the MDC value obtained when a large amount of drug is dosed can be higher for such dispersions relative to dispersions for which at least a portion of the drug is present as a drug-rich amorphous or crystalline phase.

Alternatively, the dosage form of the present invention, when tested in vitro in a physiologically relevant aqueous solution, for dissolution times of from 90 to 1200 minutes, provides an AUC value at least 1.25-fold that measured for an equivalent dosage form containing an equivalent quantity of undispersed drug. Preferably, when administered to a use environment, the dosage form also provides, for dissolution times of from 90 to 1200 minutes, an AUC value that is at least 1.25-fold that observed when an equivalent quantity of undispersed drug is dosed.

In the case of a bilayer geometry, the delivery port(s) or exit passageway(s) may be located on the side of the tablet containing the drug composition or may be on both sides of the tablet or even on the edge of the tablet so as to connect both the drug layer and the sweller layer with the exterior of the device. The exit passageway(s) may be produced by mechanical means or by laser drilling, or by creating a difficult-to-coat region on the tablet by use of special tooling during tablet compression or by other means. The rate of drug delivery from the device may be optimized so as to provide a method of delivering drug to a mammal for optimum therapeutic effect.

Osmotic systems can also be made with a homogeneous core surrounded by a semipermeable membrane coating. Drug dispersions can be incorporated into a tablet core that also contains other excipients that provide sufficient osmotic driving force and optionally solubilizing excipients such as acids or surfactant-type compounds. A semipermeable membrane coating can be applied via conventional tablet-coating techniques such as using a pan coater. A drug delivery passageway can then be formed in this coating by drilling a hole in the coating, either by use of a laser or other mechanical means. Alternatively, the passageway may be formed by rupturing a portion of the coating or by creating a region on the tablet that is difficult to coat, as described above.

Another embodiment of sustained release osmotic dosage forms of the invention includes drug dispersion-containing multiparticulates coated with a water-permeable membrane; the polymer may be dense, porous or asymmetric as described above. Such multiparticulates are prepared by, for example, melt-congealing from a spinning disk, extrusion/spheronization or fluid bed granulation, or by coating seed cores with a mixture of drug and a water-soluble polymer, as described above. Drug-containing multiparticulates may be homogeneous or layered with a drug dispersion surrounding the seed core. Following formation, such multiparticulates are then spray-coated with a substantially water-permeable coating comprising a solution of a polymer in a mixture of a solvent and, depending on the coating type desired, a non-solvent, as described above. This spray-coating operation is preferably carried out in a fluid bed coating apparatus, for example, a Glatt GPCG-5 fluid bed coater (Glatt Air, Ramsey, N.J.). The polymer used for forming the semipermeable membrane is chosen as described above.

Osmotic capsules can be made using the same or similar components to those described above for osmotic tablets and multiparticulates. The capsule shell or portion of the capsule shell can be semipermeable and made of materials described above. The capsule can then be filled either by a powder or liquid consisting of drug dispersion, excipients that imbibe water to provide osmotic potential, and/or a water-swellable polymer, or optionally solubilizing excipients. The capsule core can also be made such that it has a bilayer or multilayer composition analogous to the bilayer, trilayer or concentric geometries described above.

Another class of sustained release dosage forms useful in this invention comprises coated swellable tablets and multiparticulates, as described in EP 378 404, incorporated herein by reference. Coated swellable tablets comprise a tablet core comprising drug dispersion and a swelling material, preferably a hydrophilic polymer, coated with a membrane which contains holes or pores through which, in the aqueous use environment, the hydrophilic polymer can extrude and carry out the drug composition. Alternatively, the membrane may contain polymeric or low molecular weight water-soluble "porosigens" which dissolve in the aqueous use environment, providing pores through which the hydrophilic polymer and drug may extrude. Examples of porosigens are water-soluble polymers such as HPMC and low molecular weight compounds such as glycerol, sucrose, glucose, and sodium chloride. In addition, pores may be formed in the coating by drilling holes in the coating using a laser or other mechanical means. In this class of sustained release dosage forms, the membrane material may comprise any film-forming polymer, including polymers which are water permeable or impermeable, providing that the membrane deposited on the tablet core is porous or contains water-soluble porosigens or possesses a macroscopic hole for water ingress and drug release. Multiparticulates (or beads) may be similarly prepared, with a drug dispersion/swellable material core, coated by a porous or porosigen-containing membrane. Embodiments of this class of sustained release dosage forms may also be multilayered, as described in EP 378 404 A2.

For any of the controlled or sustained-release dosage forms mentioned above, the dosage form may additionally comprise an immediate-release layer of the same or a different drug in crystalline, amorphous or dispersion form.

The dosage forms of the present invention are useful in treating a variety of conditions and diseases including those exemplified herein, by administering the dosage forms described herein to a patient or person in need of such treatment.

EXAMPLE 1

Exemplary dosage forms of the present invention comprising a batch of solid dispersion ("SD") of 10 wt % sparingly soluble drug and 90 wt % polymer was made by mixing the drug [R-(R*,S*)]-5-chloro-N-[2-hydroxy-3-[methoxymethylamino)-3-1-(phenylmethyl)propyl]propyl]-1H-indole-2-carboxamide (a glycogen phosphorylase inhibitor) (hereinafter referred to as "Drug 1") having a water solubility of 1 µg/mL, in the solvent acetone together with a "medium fine" (MF) grade of HPMCAS (AQUOT, Shinetsu, Tokyo, Japan) to form a solution. The solution comprised 0.27 wt % Drug 1, 2.43 wt % polymer and 97.3 wt % solvent. This solution was then spray-dried by directing an atomizing spray via a rotary atomizer at 18 psi and a 100 g/min feed rate into a stainless steel chamber of a Niro portable spray-dryer maintained at 120° C. at the inlet and 68° C. at the outlet. Portions of the dispersion were held back and subjected to powder X-ray diffraction analysis and so verified the drug to be in an essentially amorphous, non-crystalline state.

The resulting solid particles had an average diameter of 5 to 20 µm. The particles were then mixed with 15 wt % of the tableting aid microcrystalline cellulose (PROSOLV, Edward Mendell Co., Patterson, N.Y.), 30 wt % of the hydrogel PEO having an average MW OF 600,000 daltons, 4 wt % of the tableting aid HPC (KLUCEL LXF, Hercules, Wilmington, Del.), 20 wt % of the osmotically effective solute lactose, and 1 wt % of the lubricant magnesium stearate and blended for 40 minutes to render the mixture homogeneous. The so-formed homogeneous core mixture contained 30 wt % of the solid dispersion, so that this core mixture contained 3 wt % Drug 1. This homogeneous core mixture was formed into tablet cores in a tableting press at approximately 4000 lbs of compressive force using 13/32-inch tooling.

The tablet cores were then coated with CA (Eastman Fine Chemicals, CA 398-10, Kingsport, Tenn.) by pan-coating the same in a coating composition comprising 7 wt % CA, 3 wt % PEG having an average MW of 3350 daltons in an acetone/water mixture (68 wt %/22 wt %) and then drying the same in a convective oven at 50° C. This coating was examined by SEM and shown to contain alternating regions of (1) thick and porous, and (2) dense and thin, generally having the morphology shown in U.S. Pat. No. 5,612,059. The finished weight of the core was 500 mg, while the dry coating weight was 79 mg (15.8 wt %). Twelve 0.9 mL diameter holes were then mechanically drilled in the coating of each tablet face to provide 24 delivery ports per tablet.

As a first control (Control A) a coated and drilled core was prepared that had the same composition in all respects except that no HPMCAS was present and the drug was in crystalline form. A second control (Control B), was prepared that consisted of the identical solid dispersion alone.

A Model Fasted Duodenum (MFD) solution was prepared to mimic the chemical environment of the small intestine, the solution comprising a phosphate-buffered saline solution containing 14.7 mM sodium taurocholic acid and 2.8 mM of 1-palmitoyl-2-oleyl-sn-glycero-3-phosphocholine with a pH of 6.5.

Figure 5:
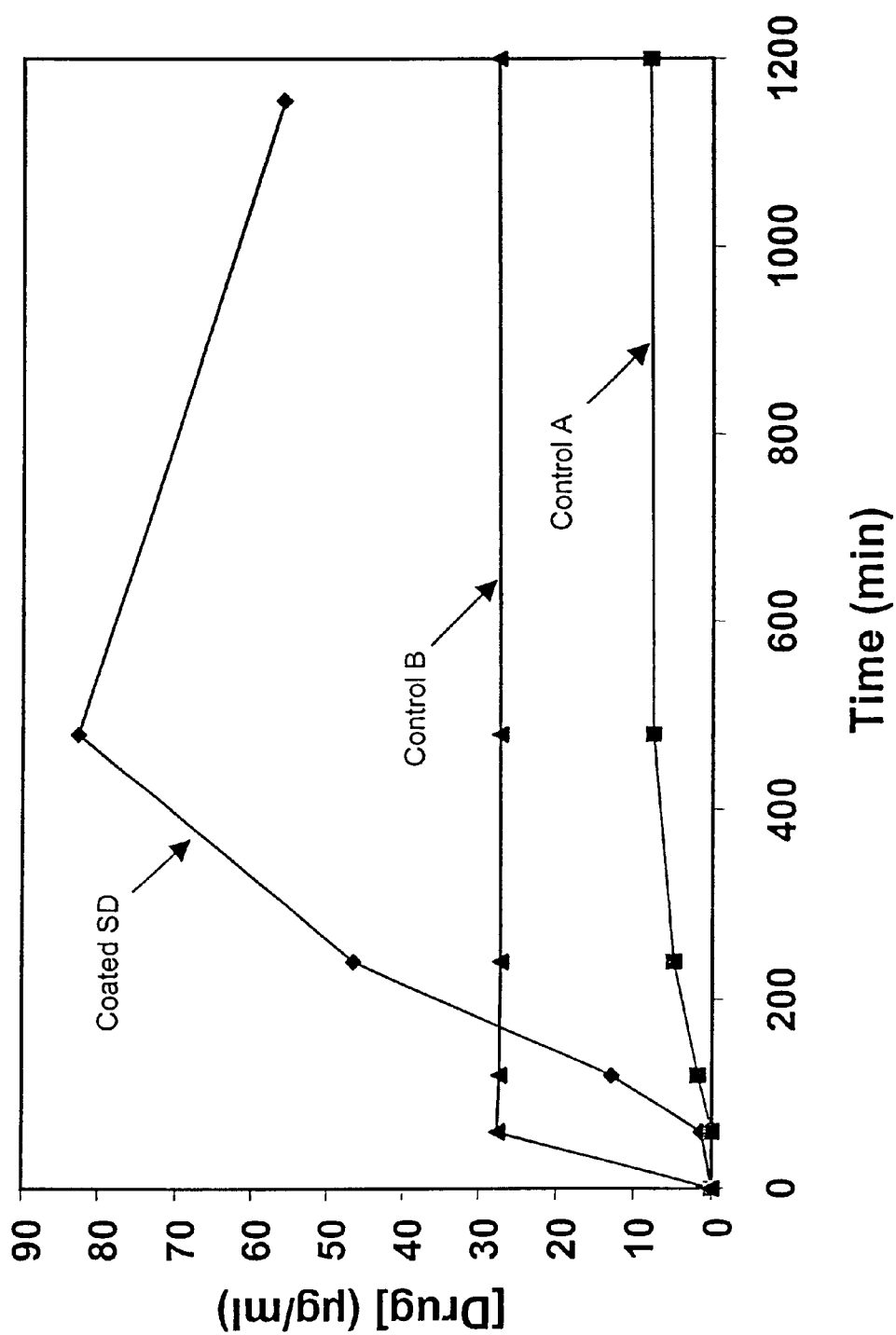
FIGS. 5–7 are graphs comprising plots of release rates of various drugs delivered by the controlled release device of the present invention and of comparative release rates for various controls.

In vitro dissolution of drug from the three dosage forms was studied by adding each of the following dosage forms to separate 50 mL aliquots of the MFD solution at 37° C.: (1) one tablet of the coated solid dispersion of the invention ("Coated SD"); (2) one tablet of Control A; and (3) 150 mg of the solid dispersion of Control B. In all three cases, the total amount of Drug 1 present was 15 mg. Thus, if all of the drug from each form dissolved, the maximum drug concentration in each test solution would be about 300 µg/mL. Drug concentration over time was determined by periodically withdrawing samples of each of the three solutions, filtering the samples to remove any undissolved drug, analyzing the samples by High Performance Liquid Chromatography (HPLC) and thereby calculating drug concentrations. The results are set forth in Table 1 and FIG. 5. As is apparent, the dosage form of the present invention exhibited dramatically higher drug concentrations over time, as well as approximately a 10-fold increase in AUC when compared to Control A.

TABLE 1

| Dosage Form Examples | Time (hrs) | [Drug]* | AUC** |
|---|---|---|---|
| Example 1 Coated SD | 1 | 1.3 | 1 |
| | 2 | 12.8 | 8 |
| | 4 | 46.5 | 67 |
| | 8 | 82.7 | 326 |
| | 19.5 | 55.9 | 1,123 |
| Control A Coated Crystalline Drug | 1 | 0 | 0 |
| | 2 | 1.8 | 1 |
| | 4 | 4.9 | 8 |
| | 8 | 7.5 | 32 |
| | 20 | 7.9 | 121 |
| Control B Dispersion only | 1 | 27.5 | 14 |
| | 2 | 27.3 | 41 |
| | 4 | 27.1 | 96 |
| | 8 | 27.2 | 206 |
| | 20 | 27.4 | 523 |

*µg/mL
**min · µg/mL

The mechanism of delivery of drug from the coated SD of the present invention (Example 1) was studied by periodic visual inspection of the tablet during drug release and revealed an imbibition of water into the core that gradually caused a swelling of the core, followed by a fairly steady extrusion of "worm"-like sections of water-swollen core material through the delivery ports, with the coating remaining intact, indicating no dissolving or eroding of the coating.

EXAMPLE 2

A solid amorphous dispersion comprising 33.3 wt % of a different glycogen phosphorylase inhibitor, namely 5-chloro-1H-indole-2-carboxylic acid[1S)-benzyl-3-((3R, 4S)-dihydroxypyrrolidin-1-yl-)-(2R)-hydroxy-3-oxypropyl] amide ("Drug 2") having a water solubility of 80 µm/mL and 66.7 wt % of the same grade of HPMCAS used in Example 1 was prepared in substantially the same way as in Example 1 except as follows: concentrations of drug and polymer in the spray solution were at 2.5 wt % and 5.0 wt %, respectively; the inlet temperature was 179° C. and the outlet temperature was 70° C.; the feed rate was 200 g/min and a 2-fluid nozzle was used. The solid dispersion thus formed was mixed with the other tableting excipients as in Example 1 such that the final composition was 28 wt % solid drug dispersion, 22 wt % xylitol containing 1.5 wt % CMC (XYLITAB 200, American Xyrofin, Shaumberg, Ill.), 29 wt % PEO having an average MW of 600,000 daltons, 20 wt % of the osmopolymer sodium starch glycolate (EXPLOTAB, Edward Mendell Co., Patterson, N.Y.) and 1 wt % magnesium stearate. Tablets from this homogeneous core mixture were prepared as in Example 1, each having a core weight of 500 mg. The substantially amorphous state of the drug in the dispersion was confirmed by powder x-ray diffraction analysis.

These cores were coated as in Example 1 with CA from a coating solution comprising 7 wt % CA, 3 wt % PEG having an average MW of 3350 daltons, 5 wt % water and 85 wt % acetone, the dry coating weight amounting to 57.5 mg (11.5 wt % of tablet core). The resulting coating was dense and substantially nonporous. Five 0.9 mL diameter delivery ports were drilled in the coating as in Example 1, for a total of 10 delivery ports for each tablet.

For a comparative dissolution study, Controls C and D were prepared. Control C comprised 280 mg of the identical solid amorphous dispersion of drug with no tableting excipients and no coating, while Control D comprised a physical mixture of 93 mg of crystalline drug and 186 mg of HPMCAS-MF.

Figure 6:
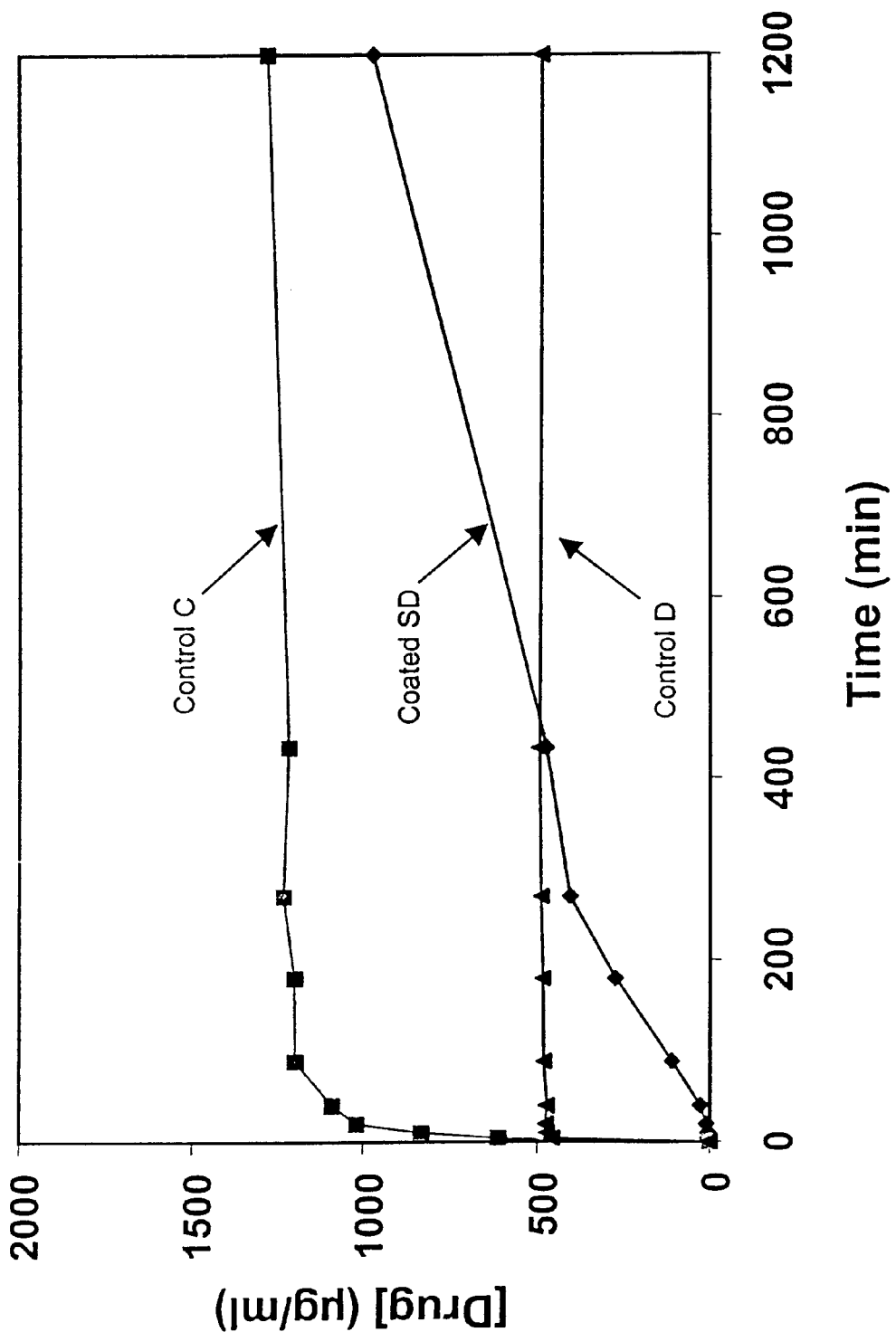
Figure 7:
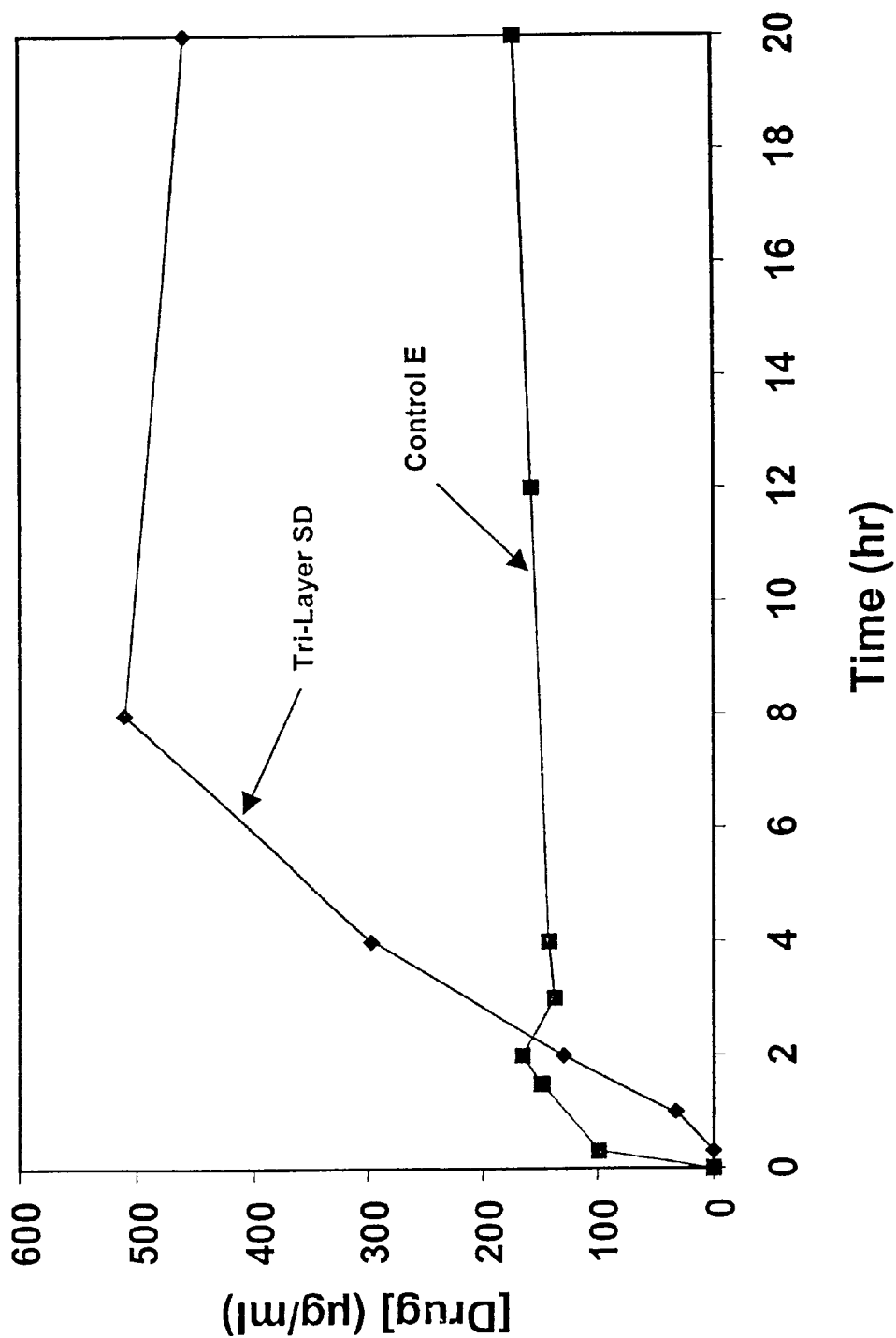

To simulate in vivo drug dissolution, two tablets of the invention and Controls C and D were first placed vin 40 mL of a simulated gastric buffer solution for 30 minutes at 37° C. and stirred, then 10 mL of MFD solution and sufficient sodium hydroxide solution to adjust the pH of the resulting solution to 6.5 were added to the gastric buffer solution. The resulting MFD solution had the same composition as that in Example 1 except that the concentrations of the taurocholic acid and the phosphocholine ester were 73.5 mM and 14 mM, respectively. Drug concentration over time was determined as in Example 1, and the results are shown in Table 2 and in the graph of FIG. 6. The data show that about 25% of the drug was released within 8 hours, and about 52% within 20 hours. This demonstrates that the dosage form of the present invention exhibits true controlled release of drug as compared to the uncoated solid drug dispersion, as the uncoated dispersion (Control C) released essentially all drug in less than an hour, generally regarded as an undesirable "spiking" of drug dosing. In addition, the concentration of drug achieved by the device of the present invention (967 $\mu$g/mL) exceeds the maximum solubility of the crystalline drug (Control D) (482 $\mu$g/mL) by a factor of two.

TABLE 2

| Dosage Form | Time (hrs) | [Drug]* | AUC** |
|---|---|---|---|
| Coated SD | 0.07 | 3.8 | 16 |
|  | 0.17 | 5.1 | 42 |
|  | 0.33 | 9.9 | 118 |
|  | 0.67 | 27.5 | 492 |
|  | 1.5 | 111 | 3,965 |
|  | 3.0 | 275 | 21,370 |
|  | 4.5 | 405 | 59,990 |
|  | 7.25 | 473 | 124,500 |
|  | 20 | 967 | 675,000 |
| Control C | 0.07 | 613 | 1,090 |
| Uncoated SD | 0.17 | 830 | 4,540 |
|  | 0.33 | 1,020 | 17,760 |
|  | 0.67 | 1,090 | 32,560 |
|  | 1.5 | 1,200 | 87,890 |
|  | 3.0 | 1,200 | 193,300 |
|  | 4.5 | 1,230 | 301,300 |
|  | 7.25 | 1,215 | 501,000 |
|  | 20 | 1,270 | 1,442,000 |
| Control D | 0.07 | 456 | 1,160 |
| Crystalline | 0.17 | 470 | 3,930 |
| Drug mixed | 0.33 | 475 | 8,660 |
| with | 0.67 | 471 | 18,110 |
| dispersion | 1.5 | 480 | 41,840 |
| polymer | 3.0 | 483 | 85,210 |
|  | 4.5 | 488 | 128,900 |
|  | 7.25 | 493 | 209,800 |
|  | 20 | 482 | 582,600 |

*$\mu$g/mL
**min · $\mu$g/mL

The mechanism of release from the coated solid dispersion of the invention was studied as in Example 1, and confirmed that the coating neither dissolved nor eroded, while the solid dispersion in the core was extruded as a solid dispersion which thereafter dissolved in the combined gastric/MFD solution.

EXAMPLE 3

This example illustrates the inventive delivery of Drug 2 except that the core of the tablet was a "trilayer" design of the type depicted in FIG. 4. The core comprised two compositions; a sweller layer between two essentially identical drug layers. The drug was in the form of a solid dispersion of identical composition to that of Example 2. The drug layers were composed of 26.25 wt % solid dispersion, 35 wt % XYLITAB 200, 32.5 wt % PEO with an average MW of 600,000 daltons, 5.0 wt % EXPLOTAB and 1.25 wt % magnesium stearate. The sweller layer was composed of 74 wt % EXPLOTAB, 25 wt % PROSOLV 90 and 1 wt % magnesium stearate. Tablets were formed by first mechanically mixing the above drug layer ingredients until homogeneous, compressing to a hardness of 4 Kponds and then milling to a size of 800 $\mu$m or less. 200 mg of the drug layer mixture were then placed into the bottom of a standard ⅜-inch die and lightly tamped. Then 100 mg of the sweller layer mixture was placed in the die on top of the drug layer and lightly tamped. Finally, an additional 200 mg of the drug layer mixture was placed in the die on top of the sweller layer. The tablet was then compressed to a hardness of 10 to 14 Kponds with the tooling described in Example 1.

The resulting trilayer core thus had a total weight of 500 mg and contained 105 mg of solid dispersion, 35 mg of which was Drug 2. The trilayer core was then coated and ports drilled as in Example 2 except that the coating weight was 11.8 wt % of the core weight.

For a comparative dissolution study, Control E, consisting of 35 mg of crystalline Drug 2 was prepared. The dissolution of drug was studied by placing two of the trilayer tablets and Control E each in 35 ml of a phosphate buffered saline (PBS) solution composed of 6 mM $KH_2PO_4$, 5 mM NaOH, 60 mM KCl and 30 mM NaCl. Drug concentration over time was determined as in Example 1 and the results are shown in Table 3. The data for the trilayer tablet is the average of the values for the two tablets tested.

The data shows that drug was gradually released from the trilayer tablet, reaching a maximum concentration after about eight hours, and demonstrating sustained release of drug. In addition, the MDC achieved by the trilayer tablet was 510 $\mu$g/mL, nearly three-fold the 171 $\mu$g/mL observed for pure crystalline drug.

TABLE 3

| Dosage Form | Time (hrs) | [Drug]* |
|---|---|---|
| Trilayer SD | 0.3 | — |
|  | 1.0 | 32 |
|  | 1.5 | — |
|  | 2.0 | 129 |
|  | 3.0 | — |
|  | 4.0 | 297 |
|  | 8.0 | 510 |
|  | 12.0 | — |
|  | 20.0 | 459 |
| Control E | 0.3 | 99 |
| Crystalline | 1.0 | — |
| Drug | 1.5 | 148 |
|  | 2.0 | 165 |
|  | 3.0 | 137 |
|  | 4.0 | 142 |
|  | 8.0 | — |
|  | 12.0 | 157 |
|  | 20.0 | 171 |

*$\mu$g/mL

EXAMPLE 4

This example illustrates a method for making a dosage form of the present invention in a bilayer core geometry of the type depicted in FIG. 2. The bilayer core consists of a drug layer and a sweller layer. To form the drug layer, the following materials may be blended and wet-granulated in a mixer: 50 g to 200 g of the drug dispersion of Example 2; 250 g to 325 g of a PEO having an average MW of about 200,000 daltons; 10 to 30 g of an HPMC having an average MW of about 11,300; and 0 to 10 g of magnesium stearate. The sweller layer may be formed by wet-granulating the following materials: 110 g to 140 g of PEO having an average MW of about 5,000,000 to 7,500,000 daltons; 5 to 25 g of an HPMC having a MW of about 11,300 daltons; 40 g to 70 g sucrose; and 0 to 10 g magnesium stearate. The bilayer core is formed by first placing 50 mg to 300 mg of the sweller layer granulation into the bottom of a ⅜-inch die and then lightly tamping the material. On top of this sweller layer is then placed 50 mg to 300 mg of the drug layer granulation. The tablet is then compressed to a hardness of 6 to 15 Kponds. The resulting bilayer cores are then coated with a semipermeable coating comprising 50% to 98% CA having an acetyl content of about .32 to 40 wt % and from 2 to 50% PEG having an average MW of about 3,350 daltons. In the coating, at least one exit passageway from 500 to 2,000 µm in diameter is formed on the drug layer face of the tablet.

EXAMPLE 5

This example illustrates the fabrication of the inventive dosage form except that the core of the device is of a concentric design of the type depicted in FIG. 3. The core consists of a sweller composition central core surrounded by the drug composition. To form the central core, 100 to 200 mg of the wet-granulated sweller mixture of Example 3 is placed in the bottom of a ¼-inch die and compressed to a hardness of about 4 to 6 Kponds. 200 to 300 mg of the drug-containing composition of Example 3 is then placed in the bottom of a ¹³⁄₃₂-inch die and leveled by hand using a spatula. The previously formed central core is then placed on top of the layer of drug-containing composition at its center and then an additional 200 to 300 mg of the same composition is placed on top of and around the central core. The material is then compressed to a hardness of 10 to 14 Kponds to form a concentric design tablet core, which is then coated with a semipermeable coating as described in Example 3. Finally, at least one exit passageway from 500 to 2,000 µm in diameter is formed on each face of the coated tablet.

EXAMPLE 6

This example illustrates the delivery of an SD of Drug 1 and HPMCAS-MF from a tablet wherein the core is of the tri-layer design depicted in FIG. 4. The core was made up of two compositions: a sweller layer between two essentially identical drug layers, each drug layer comprising an SD prepared as in Example 1, except that the SD contained 67 wt % Drug 1 and 33 wt % HPMCAS-MF.

The drug layers comprised 9.56 wt % SD, 38.4 wt % XYLITAB 200, 37.3 wt % PEO with an average MW of 600,000 daltons, 13.5 wt % EXPLOTAB, and 1.24 wt % magnesium stearate. The sweller layer was 74.5 wt % EXPLOTAB, 25 wt % microcrystalline cellulose (AVICEL PH 200, FMC Corporation, Philadelphia, Pa.) and 0.5 wt % magnesium stearate. Tablets were formed by mechanically mixing the drug layer ingredients until homogeneous. The sweller layer ingredients were then mixed until homogeneous. Tablets were formed by first placing 200 mg of the drug layer mixture in a standard ¹³⁄₃₂-inch die and tamping lightly. Then, 100 mg of the sweller layer mixture were placed in the same die on top of the first drug layer, followed by 200 mg of a second drug layer mixture, and compressing to a hardness of 10 Kp.

The resulting tri-layer core thus had a total weight of 500 mg and contained 38.25 mg of SD. The SD was determined to have a Drug 1 activity and potency of 65.4% and 90.5%, respectively. Thus, the tri-layer core contained 122.6 mg of Drug 1. The tri-layer core was then coated and ports drilled as in Example 2, except that the coating weight was 12.9% of the core weight.

For a comparative dissolution study, Control F, consisting of 22.64 mg of crystalline Drug 1, was prepared. The dissolution of drug was studied by placing two each of the tri-layer tablets and Control F preparations containing an equal amount of Drug 1 in 50 ml of the MFD solution of Example 1. Drug concentration over time was determined as in Example 1 and the results are shown in Table 4. The data for the tri-layer tablet is the average of the values for the two tablets tested.

The data show that the drug was gradually released from the tri-layer tablet, reaching a maximum concentration after about 8 hours. In addition, the MDC achieved by the tri-layer tablet was 151 µg/mL, nearly 10 times higher than the 16 µg/mL observed for the pure crystalline drug.

TABLE 4

| Dosage Form | Time (hr) | [Drug]* |
|---|---|---|
| Tri-layer Coated SD (average of 2) | 0 | 0 |
| | 2 | 51 |
| | 4 | 130 |
| | 8 | 151 |
| | 12 | 101 |
| | 20 | 57 |
| | 24 | 39 |
| Control F Crystalline Drug | 0 | 0 |
| | 2 | 13 |
| | 4 | 16 |
| | 8 | 13 |
| | 12 | 15 |
| | 20 | 12 |
| | 24 | 11 |

*µg/mL

EXAMPLE 7

This example illustrates the delivery of Drug 2 from a tablet wherein the core is of the bi-layer design shown in FIG. 2. The core comprised a sweller layer and a drug layer. The drug layer was in the form of an SD comprising 50 wt % of Drug 2 having a water solubility of 80 µg/mL and 50% HPMCAS-MF. The SD was prepared in essentially the same way as Example 1 except that the spray solution comprised 7.5 wt % Drug 2, 7.5 wt % polymer and 85 wt % 95:5 acetone:$H_2O$. This solution was spray-dried using an external mix 2-fluid atomizer with an atomizing gas feed rate of 460 g/min and a 200 g/min solution feed rate with an inlet temperature of 195° C. and an outlet temperature of 70° C.

The resulting solid particles had an average diameter of approximately 50 µm. The drug layer comprised 44.4 wt % SD, 26.1 wt % XYLITAB 200, 25.2 wt % PEO with an average MW of 600,000 daltons, 3.5 wt % EXPLOTAB, and 0.8 wt % magnesium stearate. The sweller layer was 74.5 wt % EXPLOTAB, 25 wt % PROSOLV 90, and 0.5 wt % magnesium stearate. Tablets were formed by first mechanically mixing the drug layer ingredients until homogeneous, compressing the same into lightly compacted tablets, and grinding the resulting tablets to particles less than 16 mesh in size. The sweller layer ingredients were then mixed until homogeneous. Tablets were formed by first placing 450 mg of drug layer mixture in a standard 15/32-inch die and tamping lightly, then placing 150 mg of the sweller layer mixture in the die on top of the drug layer and compressing to a hardness of 15 Kp.

The resulting bi-layer core thus had a total weight of 600 mg and contained 199.8 mg SD, 99.9 mg of which was Drug 2. This core was then coated and ports drilled as in Example 2, except that the coating weight was 8.9% of the core weight, and five 900 μm holes were drilled on the drug layer side only.

For a comparative dissolution study, Control G, consisting of 100 mg of crystalline Drug 2 was prepared. The dissolution of drug was studied by placing one each of the bi-layer tablet and Control G preparation containing an equal amount of Drug 2 in 50 ml of the phosphate-buffered solution of Example 3 (pH 7.2, osmotic pressure 5.3 atm) to simulate an intestinal environment of use. Drug concentration over time was determined as in Example 1, and the results are shown in Table 5.

The data show that the drug was gradually released from the bi-layer tablet, reaching an MDC after about 8 hours, and demonstrating sustained release of the drug. In addition, the MDC achieved by the bi-layer tablet was 608 μg/mL, nearly eight times higher than the 77 μg/mL observed for pure crystalline drug.

TABLE 5

| Dosage Form | Time (hr) | [Drug]* |
|---|---|---|
| Bi-layer Coated SD | 0 | 0 |
| | 1 | 4 |
| | 2 | 66 |
| | 4 | 350 |
| | 8 | 608 |
| | 12 | 306 |
| | 18 | 263 |
| | 24 | 298 |
| Control G Crystalline Drug | 0 | 0 |
| | 1 | 59 |
| | 2 | 72 |
| | 4 | 72 |
| | 8 | 77 |
| | 12 | 71 |
| | 18 | 71 |
| | 24 | 75 |

*μg/mL

EXAMPLE 8

Exemplary dosage forms of the present invention for sertraline (a low solubility serotonin reuptake inhibiting drug) were made with a bi-layer core geometry of the type depicted in FIG. 2. The bi-layer core consisted of a a layer of a sertraline-containing composition and a layer of a water-swellable composition. The sertraline-containing composition was in the form of a solid dispersion comprising 50 wt % of the drug and 50 wt % HPMCP-55. The solid dispersion was prepared in essentially the same way as in Example 1 except as follows: the solution comprised 2.5 wt % drug, 2.5 wt % polymer, 47.5 wt % methanol, and 47.5 wt % acetone. This solution was spray-dried using a 2-fluid nozzle with an atomization pressure of 1.8 bar and a 193 g/min feed rate. The inlet temperature maintained at 230° C. and the outlet temperature was 72° C.

The drug layer was composed of 41.15 wt % solid dispersion, 26.75 wt % XYLITAB 200, 26.75 wt % PEO with an average MW of 600,000 daltons, 4.33 wt % EXPLOTAB, and 1.02 wt % magnesium stearate. The sweller layer was composed of 74.66 wt % EXPLOTAB, 24.73 wt % PROSOLV 90, 0.47 wt % magnesium stearate, and 0.14 wt % Red Lake #40. Tablets were formed by first combining the above drug layer ingredients, precompressing, and milling in a comill at 1100 rpm (screen size 0.075 inch). The sweller layer ingredients were combined without the magnesium stearate, blended 20 minutes in a Turbula mixer, then blended again for 4 minutes with magnesium stearate. Each tablet was made using 550 mg drug layer and 150 mg sweller layer, and compressed to a hardness of 11.5 Kp.

The resulting bilayer core thus had a total weight of 700 mg and contained 226.3 mg of solid dispersion, 113.2 of which was sertraline. The bilayer core was then coated and ports drilled as previously described, except that the coating weight was 9.3% of the core weight, and one 700 μm hole was drilled.

For a comparative dissolution study, Control H, consisting of 111.4 mg of the crystalline drug, was used. The dissolution of drug was studied by placing the bilayer tablet and Control H each in 40 ml of MFD solution. Drug concentration over time was determined as in Example 1, and the results are shown in Table 6.

TABLE 6

| Dosage Form | Time (hr) | [Drug]* | AUC |
|---|---|---|---|
| Bilayer SDD | 0 | 0 | 0 |
| | 0.2 | 0 | 0 |
| | 0.3 | 0 | 0 |
| | 0.7 | 0 | 0 |
| | 1.5 | 32 | 800 |
| | 2 | 83 | 2,530 |
| | 3 | 307 | 14,250 |
| | 4 | 465 | 37,410 |
| | 6 | 566 | 99,260 |
| | 10 | 262 | 198,640 |
| | 14 | 176 | 224,940 |
| | 24 | 297 | |
| Control H Crystalline Drug | 0 | 0 | 0 |
| | 0.2 | 278 | 830 |
| | 0.3 | 401 | 4,230 |
| | 0.7 | 341 | 11,650 |
| | 1.5 | 217 | 25,610 |
| | 2 | 188 | 31,700 |
| | 3 | 168 | 42,400 |
| | 4 | 152 | 52,000 |
| | 6 | 160 | 70,640 |
| | 10 | 137 | 106,200 |
| | 14 | 135 | 122,500 |
| | 24 | 191 | |

*μg/mL
**min · μg/mL

The data shows that the drug was gradually released from the bilayer tablet, reaching a maximum concentration after about 6 hours and demonstrating sustained release of the drug. The MDC achieved by the bilayer tablet was 556 μg/mL, higher than the 401 μg/mL observed for pure crystalline drug. At 14 hours, the AUC for the bilayer tablet was 1.8 times the AUC for the control.

EXAMPLE 9

Multiparticulates that provide controlled-release of a drug formed as a solid amorphous dispersion can be made by making drug-containing cores via a melt-congealing process and then applying a water-permeable coating around these cores. To make the drug-containing cores, a drug dispersion made as in Example 1 is mixed with glyceryl behenate (COMPRITOL 888 ATO, Gattefosse Corporation, Westwood, N.J.) and PEO with an average MW of 600,000 daltons. This mixture consists of 50 wt % COMPRITOL, 25 wt % PEO, and 25 wt % drug dispersion and is mixed in a stirred and heated vessel. The mixture is heated to 85° C., melting the COMPRITOL and forming a suspension of PEO and drug dispersion. This suspension is pumped to a rotary atomizer to form droplets that solidify upon cooling to form drug dispersion-containing beads. The suspension is pumped to the rotating disc of the atomizer at a rate of about 1 kg/hr and at a rotary speed of approximately 3600 rpm. The solidified beads are collected and sieved to remove fines and any large particles or clumps.

A water-permeable coating is then applied to these beads via a conventional fluid bed coating process. A coating solution consisting of 7 wt % CA 389-10, PEG 3350, and 18 wt % water dissolved in acetone is prepared in a stirred vessel. The coating solution is spray-coated onto the beads via a bottom-spray fluid bed coater fitted with a Wurster insert. Coating solution is applied until a coating weight of approximately 15 wt % (relative to core weight) is achieved. Drug delivery ports are formed in the environment of use by imbibition of water into the bead cores, causing the core material to swell and rupture the coating. The core material is then extruded out through the rupture in the coating, providing controlled release of the drug dispersion.

EXAMPLE 10

Multiparticulates that provide controlled release of a drug formed as a solid amorphous dispersion can be made by making drug-containing cores via a spray-coating process and then applying a water-permeable coating around these cores. To make the drug-containing cores a drug solution is spray-coated onto seed cores via a conventional fluid bed coating process. The drug solution consists of 1 wt % drug, 1 wt % PEO with an average MW of 600,000 daltons, and 3 wt % HPMCAS dissolved in acetone. This drug solution is coated onto microcrystalline cellulose spheres (CELPHERE CP-507, FMC Corporation, Philadelphia, Pa.) having a nominal diameter of 600 μm in a fluid bed coater fitted with a Wurster insert. Coating is applied to the cores until a coating weight of approximately 100 wt % compared to the original weight of the cores is achieved. An amorphous drug dispersion is formed via this spray-coating process that also forms drug-containing beads.

A water-permeable coating is then applied to these beads via a conventional fluid bed coating process. A coating solution consisting of 7 wt % CA 389-10, PEG 3350, and 18 wt % water dissolved in acetone is prepared in a stirred vessel. The coating solution is spray-coated onto the beads via a bottom-spray fluid bed coater fitted with a Wurster insert. Coating solution is applied until a coating weight of approximately 15 wt % compared to the original weight of the beads is achieved. Drug delivery ports are formed in these coatings in the environment of use by imbibition of water into the bead cores, causing the core material to swell and rupture the coating. The core material is then extruded out through the rupture in the coating, providing controlled release of the drug dispersion.

The terms and expressions which have been employed in the forgoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A controlled release dosage form, comprising:
   (a) a core comprising an osmotic agent and a low solubility drug in the form of a solid dispersion of said drug in a dispersion polymer, at least a major portion of said drug being amorphous;
   (b) a water-permeable coating around said core having at least one delivery port therein, said coating controlling the influx of water to said core from an aqueous environment of use to cause extrusion of at least a portion of said core through said at least one delivery port to said aqueous environment of use, said coating being non-dissolving and non-eroding during release of said drug;
       wherein said osmotic agent comprises a water-swellable hydrophilic polymer that is separate from said dispersion polymer;
       wherein said dosage form provides an AUC in a use environment that is at least 1.25-fold that of a control dosage form comprising an identical dosage form containing an equivalent quantity of undispersed drug; and
       wherein said drug in said solid dispersion exhibits non-crystalline character in x-ray diffraction analysis.

2. The dosage form of claim 1 wherein substantially all of said drug is amorphous.

3. The dosage form of claim 1 wherein essentially all of said drug is amorphous.

4. The dosage form of claim 1 wherein said coating is a polymeric membrane.

5. The dosage form of claim 4 wherein said polymeric membrane is semipermeable.

6. The dosage form of claim 4 wherein said polymeric membrane is porous.

7. The dosage form of claim 4 wherein said polymeric membrane comprises at least one asymmetric membrane.

8. The dosage form of claim 7 wherein said at least one delivery port comprises pores in said coating.

9. The dosage form of claim 1 wherein said at least one delivery port is formed by laser drilling.

10. The dosage form of claim 1 wherein said at least one delivery port is formed in said environment of use.

11. The dosage form of claim 10 wherein said at least one delivery port is formed by the erosion of a plug of water-soluble material.

12. The dosage form of claim 10 wherein said coating is rupturable to form said at least one delivery port.

13. The dosage form of claim 12 wherein said at least one delivery port is formed by a rupture of a relatively small portion of said coating.

14. The dosage form of claim 13 wherein said rupture takes place in a thinner portion of said coating over an indentation in said core.

15. The dosage form of claim 4 wherein said coating is formed from a polymer selected from the group consisting of poly(acrylic) acids and esters; poly(methacrylic) acids and esters; copolymers of poly(acrylic) and poly (methacrylic) acids and esters; cellulose esters; cellulose ethers; and cellulose ester/ethers.

16. The dosage form of claim 4 wherein said coating is formed from a polymer selected from the group consisting of polyethylene glycol, polypropylene glycol, copolymers of polyethylene glycol and polypropylene glycol, poly (vinylpyrrolidone), ethyl cellulose, hydroxyethyl cellulose, hydroxypropyl cellulose, carboxymethyl cellulose, carboxymethylethyl cellulose, starch, dextran, dextrin, chitosan, collagen, gelatin, bromelain, cellulose acetate, unplasticized cellulose acetate, plasticized cellulose acetate, reinforced cellulose acetate, cellulose acetate phthalate, cellulose acetate trimellitate, hydroxypropylmethylcellulose, hydroxypropylmethyl-cellulose phthalate, hydroxypropylmethylcellulose acetate succinate, hydroxypropylmethylcellulose acetate trimellitate, cellulose nitrate, cellulose diacetate, cellulose triacetate, agar acetate, amylose triacetate, beta glucan acetate, beta glucan triacetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxlated ethylene-vinylacetate, cellulose acetate butyrate, polyalkenes, polyethers, polysulfones, polyethersulfones, polystyrenes, polyvinyl halides, polyvinyl esters and ethers, natural waxes and synthetic waxes.

17. The dosage form of claim 1 in a form selected from the group consisting of a tablet, a capsule a bead and a collection of at least two types of beads having different drug release properties, and wherein the environment of use is a human gastrointestinal tract.

18. The dosage form of claim 1 further comprising an osmotically effective solute.

19. A controlled release dosage form, comprising:
   (a) a core comprising an osmotic agent and a low solubility drug in the form of a solid dispersion of said drug in a dispersion polymer, at least a major portion of said drug being amorphous;
   (b) a water-permeable coating around said core having at least one delivery port therein, said coating controlling the influx of water to said core from an aqueous environment of use to cause extrusion of at least a portion of said core through said at least one delivery port to said aqueous environment of use, said coating being non-dissolving and non-eroding during release of said drug
      wherein said osmotic agent comprises a water-swellable hydrophilic polymer that is separate from said dispersion polymer;
      wherein said dosage form provides an AUC in a use environment that is at least 1.25-fold that of a control dosage form comprising an identical dosage form containing an equivalent quantity of undispersed drug;
      wherein said osmotic agent is segregated from said solid dispersion and;
      wherein said drug in said solid dispersion exhibits non-crystalline character in x-ray diffraction analysis.

20. The dosage form of claim 19 wherein said osmotic agent and said solid dispersion are in respective discrete layers.

21. The dosage form of claim 20 wherein said osmotic agent is in a first layer and said solid dispersion is in a second layer.

22. The dosage form of claim 21, including solid dispersion in a third layer wherein said osmotic agent is between said first layer and said second layer.

23. The dosage form of claim 19 wherein said solid dispersion surrounds said osmotic agent.

24. The dosage form of claim 18 wherein said water-swellable hydrophilic polymer is selected from the group consisting of hydrophilic vinyl and acrylic polymers, polysaccharide alginates, poly(ethylene oxide), polyethylene glycol, polypropylene glycol, poly(2-hydroxyethyl methacrylate), poly(acrylic) acid, poly(methacrylic) acid, polyvinyl pyrrolidone, crosslinked polyvinyl pyrrolidone, polyvinyl alcohol, polyvinyl pyrrolidone/polyvinyl alcohol copolymers, vinyl acetate, hydrophilic polyurethanes containing large polyethylene oxide blocks, carrageenan, hydroxethyl-cellulose, hydroxypropylcellulose, hydroxypropylmethyl-cellulose, carboxymethylcellulose, carboxyethylcellulose, sodium alginate, polycarbophil, gelatin, xanthan gum, sodium croscarmellose, and sodium starch glycolate.

25. The dosage form of claim 24 wherein said water-swellable hydrophilic polymer is selected from the group consisting of polyethylene oxide, polyethylene glycol, carboxymethylcellulose, polyvinyl pyrrolidone, hydroxypropylmethylcellulose, poly(acrylic) acid, cross-linked poly(acrylic) acid, sodium croscarmellose and sodium starch glycolate.

26. The dosage form of claim 1 wherein said core further comprises a solubility-enhancing agent.

27. The dosage form of claim 26 wherein said solubility-enhancing agent is selected from the group consisting of organic acids and organic acid salts; partial glycerides; glycerides; glyceride derivatives; polyethylene glycol esters; polypropylene glycol esters; polyhydric alcohol esters; polyoxyethylene ethers; sorbitan esters; polyoxyethylene sorbitan esters; carbonate salts; and cyclodextrins.

28. The dosage form of claim 1 wherein said solid dispersion is formed by spray-drying.

29. The dosage form of claim 1 wherein said dispersion polymer is selected from the group consisting of:
   (a) ionizable cellulosic polymers;
   (b) nonionizable cellulosic polymers; and
   (c) vinyl polymers and copolymers having substituents selected from the group consisting of hydroxyl, alkylacyloxy and cyclicamido.

30. The dosage form of claim 1 wherein said dispersion polymer is selected from the group consisting of hydroxypropylmethyl-cellulose, hydroxypropylmethylcellulose phthalate, hydroxypropylmethylcellulose acetate succinate, hydroxypropylmethylcellulose acetate phthalate, cellulose acetate phthalate, cellulose acetate trimellitate, polyvinyl pyrrolidone, polyvinyl alcohol, and copolymers of polyvinyl pyrrolidone and polyvinyl alcohol.

31. The dosage form of claim 28 wherein, prior to formation of said solid dispersion, said drug is amorphous.

32. The dosage form of claim 28 wherein, prior to formation of said solid dispersion, said drug is crystalline.

33. The dosage form of claim 1 wherein said core further comprises excipients.

34. The dosage form of claim 33 wherein said excipients are selected from the group consisting of surfactants, water-soluble polymers, pH modifiers, fillers, binders, pigments, lubricants, antioxidants and flavorants.

35. The dosage form of claim 1 wherein said dosage form provides a maximum concentration of said drug in a use environment that is at least 1.2-fold that of a control dosage form comprising an identical dosage form containing an equivalent quantity of undispersed drug.

36. The dosage form of claim 1 wherein said dosage form is dosed orally to a mammal, said dosage form provides an AUC in drug concentration in the blood that is at least 1.25-fold that of a control dosage form comprising an identical dosage form except containing an equivalent quantity of undispersed drug.

37. The dosage form of claim 36 wherein said dosage form provides a maximum drug concentration in the blood at a $t_{max}$ which is at least 30 minutes longer but not more than 24 hours longer than the $t_{max}$ observed for said control dosage form.

38. The dosage form of claim 1 wherein said drug is selected from the group consisting of an anti-hypertensive, and antianxiety agent, an anticlotting agent, a blood glucose-lowering agent, a decongestant, an antihistamine, an antitussive, an anti-inflammatory, an anti-atherosclerotic agent, an antipsychotic agent, a cognitive enhancer, a cholesterol-reducing agent, an antiobesity agent, an autoimmune disorders agent, a hypnotic agent, an anti-Parkinsonism agent, an antibiotic, an antiviral agent, an anti-impotence agent, an anti-neoplastic, a sedative, a barbituate, a nutritional agent, a beta-blocker, an emetic, an anti-emetic, a diuretic, an anticoagulant, a cardiotonic, an androgen, a corticoid, an anabolic agent, an anti-depression agent, an anti-infective agent, a coronary vasodilator, a carbonic anhydrase inhibitor, an antifungal, an antiprotozoal, a gastrointestinal agent, a dopaminergic agent, an anti-Alzheimer's Disease agent, an anti-ulcer agent, a platelet inhibitor, and a glycogen phosphorylase inhibitor.

39. The dosage form of claim 38 wherein said drug is an antihypertensive selected from the group consisting of prazosin, nifedipine, trimazosin and doxazosin.

40. The dosage form of claim 38 wherein said drug is the antipsychotic agent ziprasidone.

41. The dosage form of claim 38 wherein said drug is the blood glucose-lowering agent glipizide.

42. The dosage form of claim 38 wherein said drug is an anti-impotence agent selected from the group consisting of sildenafil and pharmaceutically acceptable salts thereof.

43. The dosage form of claim 38 wherein said drug is the anti-inflammatory agent (+)-N-{4-[3-(4-fluorophenoxy) phenoxy]-2-cyclopenten-1-yl}-N-hyroxyurea.

44. The dosage form of claim 38 wherein said drug is an antidepression agent selected from the group consisting of fluoxetine, paroxetine, venlafaxine, sertraline, [3,6-Dimethyl-2-(2,4,6-trimethyl-phenoxy)-pyridin4-yl]-(1-ethylpropyl)-amine and 3,5-dimethyl-4-(3'-pentoxy)-2-(2', 4',6'-trimethylphenoxy)pyridine.

45. The dosage form of claim 38 wherein said drug is a glycogen phosphorylase inhibitor selected from the group consisting of [R-(R*S*)]-5-chloro-N-[2-hydroxy-3-[methoxymethylamino}-3-oxo-1-(phenylmethyl)propyl]-propyl]-1H-indole-2-carboxamide and 5-chloro-1H-indole-2-carboxylic acid [(1S)-benzl;-3((3R,4S)-dihydroxypyrrolidin-1-yl-)-(2R)-hydroxy-3-oxypropyl] amide.

46. A method of treating a disease or disorder in a person comprising administering to said person a dosage form comprising:
  (a) a core comprising an osmotic agent and a low solubility drug in the form of a solid dispersion of said drug in a dispersion polymer, at least a major portion of said drug being amorphous polymer; and
  (b) a water-permeable coating around said core having at least one delivery port therein, said coating controlling the influx of water to said core from an aqueous environment of use to cause extrusion of at least a portion of said core through said at least one delivery port to said aqueous environment of use, said coating being non-dissolving and non-eroding during release of said drug
  wherein said dosage form provides an AUC in a use environment that is at least 1.25-fold that of a control dosage form comprising an identical dosage form containing an equivalent quantity of undispersed drug; and wherein said drug in said solid dispersion exhibits non-crystalline character in x-ray diffraction analysis.

47. The dosage form of claim 1 wherein said solid dispersion is homogeneous.

48. The dosage form of claim 1 wherein said dispersion polymer is hydroxypropylmethyl cellulose acetate succinate.

49. The dosage form of claim 19 wherein substantially all of said drug is amorphous.

50. The dosage form of claim 19 wherein essentially all of said drug is amorphous.

51. The dosage form of claim 19 wherein said coating is a polymeric membrane.

52. The dosage form of claim 19 in a form selected from the group consisting of a tablet, a capsule a bead and a collection of at least two types of beads having different drug release properties, and wherein the environment of use is a human gastrointestinal tract.

53. The dosage form of claim 19 wherein said core further comprises an osmotically effective solute.

54. The dosage form of claim 19 wherein said water-swellable hydrophilic polymer is selected from the group consisting of hydrophilic vinyl and acrylic polymers, polysaccharide alginates, poly(ethylene oxide), polyethylene glycol, polypropylene glycol, poly(2-hydroxyethyl methacrylate), poly(acrylic) acid, poly(methacrylic) acid, polyvinyl pyrrolidone, crosslinked polyvinyl pyrrolidone, polyvinyl alcohol, polyvinyl pyrrolidone/polyvinyl alcohol copolymers, vinyl acetate, hydrophilic polyurethanes containing large polyethylene oxide blocks, carrageenan, hydroxethyl-cellulose, hydroxypropylcellulose, hydroxypropylmethyl-cellulose, carboxymethylcellulose, carboxyethylcellulose, sodium alginate, polycarbophil, gelatin, xanthan gum, sodium croscarmellose, and sodium starch glycolate.

55. The dosage form of claim 54 wherein said water-swellable hydrophilic polymer is selected from the group consisting of polyethylene oxide, polyethylene glycol, carboxymethylcellulose, polyvinyl pyrrolidone, hydroxypropylmethylcellulose, poly(acrylic) acid, cross-linked poly(acrylic) acid, sodium croscarmellose and sodium starch glycolate.

56. The dosage form of claim 19 wherein said core further comprises a solubility-enhancing agent.

57. The dosage form of claim 56 wherein said solubility-enhancing agent is selected from the group consisting of organic acids and organic acid salts; partial glycerides; glycerides; glyceride derivatives; polyethylene glycol esters; polypropylene glycol esters; polyhydric alcohol esters; polyoxyethylene ethers; sorbitan esters; polyoxyethylene sorbitan esters; carbonate salts; and cyclodextrins.

58. The dosage form of claim 19 wherein said solid dispersion is formed by spray-drying.

59. The dosage form of claim 19 wherein said dispersion polymer is selected from the group consisting of:
  (a) ionizable cellulosic polymers;
  (b) nonionizable cellulosic polymers; and
  (c) vinyl polymers and copolymers having substituents selected from the group consisting of hydroxyl, alkylacyloxy and cyclicamido.

60. The dosage form of claim 59 wherein said dispersion polymer comprises hydroxypropylmethyl-cellulose, hydroxypropylmethylcellulose phthalate, hydroxypropylmethylcellulose acetate succinate, hydroxypropylmethylcellulose acetate phthalate, cellulose acetate phthalate, cellulose acetate trimellitate, polyvinyl pyrrolidone, polyvinyl alcohol, and copolymers of polyvinyl pyrrolidone and polyvinyl alcohol.

61. The dosage form of claim 58 wherein, prior to formation of said solid dispersion, said drug is amorphous.

62. The dosage form of claim 58 wherein, prior to formation of said solid dispersion, said drug is crystalline.

63. The dosage form of claim 19 wherein said core further comprises excipients.

64. The dosage form of claim 63 wherein said excipients are selected from the group consisting of surfactants, water-soluble polymers, pH modifiers, fillers, binders, pigments, lubricants, antioxidants and flavorants.

65. The dosage form of claim 19 wherein said dosage form provides a maximum concentration of said drug in a use environment that is at least 1.2-fold that of said control dosage form.

66. The dosage form of claim 19 wherein said dosage form is dosed orally to a mammal, said dosage form provides an AUC in drug concentration in the blood that is at least 1.25-fold that of said control dosage form.

67. The dosage form of claim 66 wherein said dosage form provides a maximum drug concentration in the blood at a $t_{max}$ which is at least 30 minutes longer but not more than 24 hours longer than the $t_{max}$ observed for said control dosage form.

68. The dosage form of claim 19 wherein said drug is selected from the group consisting of an anti-hypertensive, and antianxiety agent, an anticlotting agent, a blood glucose-lowering agent, a decongestant, an antihistamine, an antitussive, an anti-inflammatory, an anti-atherosclerotic agent, an antipsychotic agent, a cognitive enhancer, a cholesterol-reducing agent, an antiobesity agent, an autoimmune disorders agent, a hypnotic agent, an anti-Parkinsonism agent, an antibiotic, an antiviral agent, an anti-impotence agent, an anti-neoplastic, a sedative, a barbituate, a nutritional agent, a beta-blocker, an emetic, an anti-emetic, a diuretic, an anticoagulant, a cardiotonic, an androgen, a corticoid, an anabolic agent, an anti-depression agent, an anti-infective agent, a coronary vasodilator, a carbonic anhydrase inhibitor, an antifungal, an antiprotozoal, a gastrointestinal agent, a dopaminergic agent, an anti-Alzheimer's Disease agent, an anti-ulcer agent, a platelet inhibitor, and a glycogen phosphorylase inhibitor.

69. The dosage form of claim 68 wherein said drug is the antipsychotic agent ziprasidone.

70. The dosage form of claim 19 wherein said solid dispersion is homogeneous.

71. The dosage form of claim 19 wherein said dispersion polymer is hydroxypropylmethyl cellulose acetate succinate.

* * * * *